United States Patent
Ben et al.

(10) Patent No.: US 12,115,184 B2
(45) Date of Patent: *Oct. 15, 2024

(54) AMORPHOUS CALCIUM CARBONATE STABILIZED WITH POLYPHOSPHATES OR BISPHOSPHONATES

(71) Applicant: AMORPHICAL LTD., Ness Ziona (IL)

(72) Inventors: Yosef Ben, Arava (IL); Yigal Dov Blum, San Jose, CA (US); Hagay Moshe, Giv'at Shmuel (IL); Ben Ashkenazi, Be'er-Sheba (IL)

(73) Assignee: AMORPHICAL LTD., Ness Ziona, IL (US)

( * ) Notice: Subject to any disclaimer, the term of this patent is extended or adjusted under 35 U.S.C. 154(b) by 640 days.

This patent is subject to a terminal disclaimer.

(21) Appl. No.: 17/343,471

(22) Filed: Jun. 9, 2021

(65) Prior Publication Data

US 2021/0308178 A1 Oct. 7, 2021

Related U.S. Application Data

(62) Division of application No. 15/579,010, filed as application No. PCT/IL2016/050572 on Jun. 2, 2016, now Pat. No. 11,052,107.

(60) Provisional application No. 62/170,712, filed on Jun. 4, 2015.

(51) Int. Cl.
| | | |
|---|---|---|
| A61K 33/10 | (2006.01) | |
| A61K 9/00 | (2006.01) | |
| A61K 9/10 | (2006.01) | |
| A61K 9/14 | (2006.01) | |
| A61K 47/24 | (2006.01) | |
| A61P 31/00 | (2006.01) | |
| A61P 35/00 | (2006.01) | |

(52) U.S. Cl.
CPC ............ *A61K 33/10* (2013.01); *A61K 9/0019* (2013.01); *A61K 9/0056* (2013.01); *A61K 9/0073* (2013.01); *A61K 9/10* (2013.01); *A61K 9/143* (2013.01); *A61K 47/24* (2013.01); *A61P 31/00* (2018.01); *A61P 35/00* (2018.01)

(58) Field of Classification Search
CPC .... A61K 33/10; A61K 9/0019; A61K 9/0056; A61K 9/0073; A61K 9/10; A61K 9/143; A61K 9/14; A61K 9/20; A61K 47/24; A61K 47/02; A61K 8/19; A61K 9/006; A61K 9/19; A61P 31/00; A61P 35/00; A61Q 19/00

See application file for complete search history.

(56) References Cited

U.S. PATENT DOCUMENTS

| | | |
|---|---|---|
| 4,199,496 A | 4/1980 | Johnson |
| 4,237,147 A | 12/1980 | Merten |
| 4,964,894 A | 10/1990 | Freepons |
| 5,437,857 A | 8/1995 | Tung |
| 5,886,012 A | 3/1999 | Pang |
| 6,265,200 B1 | 7/2001 | De Leys |
| 6,348,571 B1 | 2/2002 | Redei |
| 8,324,301 B2 | 12/2012 | Cavalier |
| 8,728,533 B2 | 5/2014 | Ben |
| 8,802,160 B2 | 8/2014 | Bentov |
| 8,906,996 B2 | 12/2014 | Vucak |
| 9,149,494 B2 | 10/2015 | Sagi |
| 9,550,878 B2 | 1/2017 | Meiron |
| 2003/0077604 A1 | 4/2003 | Sun |
| 2004/0028748 A1 | 2/2004 | Sasaya |
| 2004/0234614 A1 | 11/2004 | Strong |
| 2006/0165784 A1 | 7/2006 | Zhao |
| 2007/0041506 A1 | 2/2007 | Bottino |
| 2007/0191963 A1 | 8/2007 | Winterbottom |
| 2008/0095819 A1 | 4/2008 | Gourdie |
| 2010/0096330 A1 | 4/2010 | Gotch |
| 2013/0190441 A1 | 7/2013 | Vucak |
| 2015/0056306 A1 | 2/2015 | Sagi et al. |

FOREIGN PATENT DOCUMENTS

| | | |
|---|---|---|
| CA | 2806131 | 2/2012 |
| CN | 101314031 | 12/2008 |
| CN | 101580260 | 11/2009 |
| CN | 101969962 | 2/2011 |
| CN | 102085356 | 6/2011 |
| CN | 103663532 B | 10/2015 |
| EP | 0052677 | 6/1982 |
| EP | 1666046 | 6/2006 |
| GB | 2217988 | 11/1989 |
| JP | H099871 | 1/1997 |

(Continued)

OTHER PUBLICATIONS

Addadi et al., (2003) Taking advantage of disorder: amorphous calcium carbonate and its roles in biomineralization. Advanced Materials 15(12):959-970.

Amjad & Hooley, (1994) Effect of antiscalants on the precipitation of calcium carbonate in aqueous solutions. Tenside, surfactants, detergents, 31(1), 12-17.

Bajpai et al., (2004) Pseudohypoparathyroidism Presenting with Bony Deformities Resembling Rickets. Indian Journal of Pediatrics 71(4):345-347.

(Continued)

*Primary Examiner* — Zohreh A Fay

(74) *Attorney, Agent, or Firm* — Dorsey & Whitney LLP

(57) ABSTRACT

The present invention provides solid compositions of amorphous calcium carbonate (ACC) and a polyphosphate, bisphosphonate or pharmaceutical salts thereof as a stabilizer. Said stabilizers stabilizes the ACC and prevent crystallization to crystalline calcium carbonate (CCC) for a long period of time, even in an aqueous suspension. The invention further provides pharmaceutical composition comprising the solid ACC compositions as well their use in treating of certain diseases and conditions.

4 Claims, 9 Drawing Sheets

(56) References Cited

FOREIGN PATENT DOCUMENTS

| | | |
|---|---|---|
| JP | H01156985 | 9/1998 |
| JP | H10236957 | 9/1998 |
| JP | 2002504140 | 2/2002 |
| JP | 2003292453 | 10/2003 |
| JP | 2004081739 | 3/2004 |
| JP | 2008500332 | 1/2008 |
| JP | 2008545845 A | 12/2008 |
| JP | 2011501676 | 1/2011 |
| KR | 1020050110119 | 11/2005 |
| KZ | 26035 A4 | 9/2012 |
| RU | 2550865 C1 | 5/2015 |
| WO | 9724069 | 7/1997 |
| WO | 9857656 | 12/1998 |
| WO | 2005025581 | 3/2005 |
| WO | 2005115414 | 12/2005 |
| WO | 2006043966 | 4/2006 |
| WO | 2006131497 A1 | 12/2006 |
| WO | 2007048811 | 5/2007 |
| WO | 2008041236 | 4/2008 |
| WO | 2009053967 | 4/2009 |
| WO | 2009087553 | 7/2009 |
| WO | 2012149173 | 11/2012 |
| WO | 2013088440 | 6/2013 |
| WO | 2014024191 | 2/2014 |
| WO | 2014122658 | 8/2014 |
| WO | 2016016893 A1 | 2/2016 |
| WO | 2016016895 A1 | 2/2016 |

OTHER PUBLICATIONS

Ben-Aharon et al., (2013) Bisphosphonates in the adjuvant setting of breast cancer therapy—effect on survival: a systematic review and meta-analysis. PloS one, 8(8), e70044.
Bentov et al., (2010) Stabilization of amorphous calcium carbonate by phosphate rich organic matrix proteins and by single phosphoamino acids. Journal of structural biology, 171(2), 207-215.
Buehrer & Reitemeier, (1940) The Inhibiting Action of Minute Amounts of Sodium Hexametaphosphate on the Precipitation of Calcium Carbonate from Ammoniacal Solutions. II. Mechanism of the Process, with Special Reference to the Formation of Calcium Carbonate Crystals. The Journal of Physical Chemistry, 44(5), 552-574.
Chen et al., (2013) Ethanol assisted synthesis of pure and stable amorphous calcium carbonate nanoparticles. Chemical Communications, 49(83), 9564-9566.
Chick & Borah, (1990) Calcium carbonate gel therapy for hydrofluoric acid burns of the hand. Plastic and Reconstructive Surgery 86(5):935-940.
Clarkson et al., (1992) Role of metastable phases in the spontaneous precipitation of calcium carbonate. Journal of the Chemical Society, Faraday Transactions, 88(2), 243-249.
Database Uniprot P98157 (1996) Internet site http://www.uniprot.org/uniprot/P98157.html—last modified Nov. 30, 2010—22 pages.
Database WPI Week 200432 Thomson Scientific, London, GB; AN 343036 XP002512142 & JP 2004 081739 A (Bankoku Needle Mfg) Mar. 18, 2004 (Mar. 18, 2004) & JP 2004 081739 A (Akashi Mitsuru; Tabata Masashi; Biomedical Technology Hybrid L) Mar. 18, 2004 (Mar. 18, 2004).
Gal et al., (1996) Calcium carbonate solubility: a reappraisal of scale formation and inhibition. Talanta, 43(9), 1497-1509.
GenCore Database, (2012) DQ847548. 3 pages.
Glimcher (1984) Recent studies of the mineral phase in bone and its possible linkage to the organic matrix by protein-bound phosphate bonds. Philos Trans R Soc Lond B Biol Sci 304(1121): 479-508.
Halloran and Donachy (1995) Characterization of organic matrix macromolecules from the shells of the Antarctic scallop, *Adamussium colbecki*. Comp Biochem Physiol B Biochem Mol Biol 111(2): 221-231.
Hecker et al., (2003) Phosphorylation of serine residues is fundamental for the calcium-binding ability of Orchestin, a soluble matrix protein from crustacean calcium storage structures. FEBS Lett 535(1-3): 49-54.

Huang et al., (2007) A carbonate controlled-addition method for amorphous calcium carbonate spheres stabilized by poly (acrylic acid) s. Langmuir, 23(24), 12086-12095.
Inoue et al., (2001) Purification and structural determination of a phosphorylated peptide with anti-calcification and chitin-binding activities in the exoskeleton of the crayfish, *Procambarus clarkii*. Biosci Biotechnol Biochem 65(8): 1840-1848.
Inoue et al., (2007) Significance of the N- and C-terminal regions of CAP-1, a cuticle calcification-associated peptide from the exoskeleton of the crayfish, for calcification. Peptides 28(3): 566-573.
Ishii et al., (1998) Solubilization and Chemical Characterization of an Insoluble Matrix Protein in the Gastroliths of a Crayfish, *Procambarus clarkii*, Biosci Biotechnol Biochem, vol. 62(2): 291-296 4 pages.
Kavanagh et al., (1990) Inhibitor effects on calcite growth at low supersaturations. Journal of the Chemical Society, Faraday Transactions, 86(6), 965-972.
Lee et al., (2005) Fabrication of unusually stable amorphous calcium carbonate in an ethanol medium. Materials Chemistry and Physics 93(2-3): 376-382.
Lin & Singer, (2005) Inhibition of calcite crystal growth by polyphosphates. Water Research, 39(19), 4835-4843.
Luquet and Marin (2004) Biomineralisations in crustaceans: storage strategies. Comptes Rendus Palevol 3(6-7): 515-534.
Ma et al., (2007) A novel extrapallial fluid protein controls the morphology of nacre lamellae in the pearl oyster, *Pinctada fucata*. J Biol Chem 282(32): 23253-23263.
Meiron et al., (2011) Solubility and bioavailability of stabilized amorphous calcium carbonate. Journal of Bone and Mineral Research, 26(2), 364-372.
Melanoma skin cancer (2013) American Cancer Society. 3 pages.
Müller et al., (2015) Nonenzymatic Transformation of Amorphous CaCO3 into Calcium Phosphate Mineral after Exposure to Sodium Phosphate in Vitro: Implications for in Vivo Hydroxyapatite Bone Formation. ChemBioChem, 16(9), 1323-1332.
Multigner et al., (1983) Pancreatic stone protein, a phosphoprotein which inhibits calcium carbonate precipitation from human pancreatic juice. Biochemical And Biophysical Research Communications 110(1): 69-74.
Nakatsuji et al., (2000) Changes in the Amounts of the Molt-Inhibiting Hormone in Sinus Glands during the Molt Cycle of the American Crayfish, *Procambarus clarkii*. Zoolog Sci 17(8): 1129-1136.
Nebel et al., (2008) On the structure of amorphous calcium carbonate—A detailed study by solid-state NMR spectroscopy. Inorganic Chemistry, 47(17), 7874-7879.
Non-Hodgkin lymphoma, (2012) American Cancer Society. 5 pages.
Ogino et al., (1988) Effect of Polyamine-N-Polyphosphonic Acid on the Formation and the Transformation of Calcium-Carbonate. Nippon Kagaku Kaishi, (6), 899-905.
OsteoPhase, (2011) Tango advanced Nutrition—Healthy Bone Support Formula. 3 pages.
Osteoporosis, (2005) How to strengthen your bones and prevent fractures. The healthier Life. 3 pages.
Qi et al., (2014) Atp-stabilized amorphous calcium carbonate nanospheres and their application in protein adsorption. Small, 10(10), 2047-2056.
Raz et al., (2002) Stable amorphous calcium carbonate is the main component of the calcium storage structures of the crustacean *Orchestia cavimana*. Biol Bull 203: 269-274.
Rodriguez-Blanco et al., (2008) How to make 'stable'ACC: protocol and preliminary structural characterization. Mineralogical Magazine, 72(1), 283-286.
Saitoh et al., (1985) Inhibition of calcium-carbonate precipitation by human salivary proline-rich phosphoproteins. Arch Oral Biol 30(8): 641-643.
Sawada, (1997) The mechanisms of crystallization and transformation of calcium carbonates. Pure and Applied Chemistry, 69(5), 921-928.
Shechter et al., (2008) A gastrolith protein serving a dual role in the formation of an amorphous mineral containing extracellular matrix. Proc Natl Acad Sci U S A 105(20): 7129-7134.
Spiegel et al., (1983) Group therapy and hypnosis reduce metastatic breast carcinoma pain. Psychosomatic Medicine.; 45(4):333-339.

(56) References Cited

OTHER PUBLICATIONS

Sugawara et al., (2006) Self-Organization of Oriented Calcium Carbonate/Polymer Composites: Effects of a Matrix Peptide Isolated from the Exoskeleton of a Crayfish. Angewandte Chemie International Edition, 45(18), 2876-2879.
Sugawara et al., (2006) Supporting information. Angewandte Chemie International Edition, 45(18), S1-S5.
Takagi et al., (2000) Immunolocalization of gastrolith matrix protein (GAMP) in the gastroliths and exoskeleton of crayfish, *Procambarus clarkii*. Zoological Science 17: 179-184.
Thys-Jacobs et al., (1998) Calcium carbonate and the premenstrual syndrome: Effects on premenstrual and menstrual symptoms. American Journal of Obstetrics and Gynecology 179(2):444-452.
Tlili et al., (2002) Characterization of CaCO3 hydrates by micro-Raman spectroscopy. Journal of Raman spectroscopy, 33(1), 10-16.
Tolba et al., (2016) High biocompatibility and improved osteogenic potential of amorphous calcium carbonate/vaterite. Journal of Materials Chemistry B, 4(3), 376-386.
Travis (1960) The Deposition of Skeletal Structures in the Crustacea. I. The Histology of the Gastrolith Skeletal Tissue Complex and the Gastrolith in the Crayfish, *Orconectes (cambarus) virllis* Hagen—Decapoda. Biol Bull 118: 137-149.
Travis (1963) Structural features of mineralization from tissue to macromolecular levels of organization in the decapod Crustacea. Ann N Y Acad Sci 109: 177-245.
Tsutsui et al., (1999) Cloning and expression of a cDNA encoding an insoluble matrix protein in the gastroliths of a crayfish, *Procambarus clarkia*. Zoological Science (Tokyo) 16(4): 619-628.
Ueno and Mizuhira (1984) Calcium transport mechanism in crayfish gastrolith epithelium correlated with the molting cycle. II. Cytochemical demonstration of Ca2+-ATPase and Mg2+-ATPase. Histochemistry 80(3): 213-217.
Väisänen, (2011) CaCO3 scale inhibition in paper making processes—evaluation of testing methods and inhibitor performance. Master of science thesis, 1-95.
Withnall (2000) Biology of Yabbies (*Cherax destructor*), Aquaculture Information Notes, Department of Primary Industries, 6 pages.
Wolf & Günther, (2001) Thermophysical investigations of the polymorphous phases of calcium carbonate. Journal of thermal analysis and calorimetry, 65(3), 687-698.
Xu et al., (2005) Stable amorphous CaCO3 microparticles with hollow spherical superstructures stabilized by phytic acid. Advanced Materials, 17(18), 2217-2221.
Xurong et al., (2008) Amorphous Calcium Carbonate in Biomineralization. Progress in Chemistry 20(1): 54-59.
Yudkovsky (2007) Hepatopancreatic multi-transcript expression patterns in the crayfish *Cherax quadricarinatus* during the moult cycle. Insect Molecular Biology 16(6): 661-674.
Akiva-Tal et al., (2011) In situ molecular NMR picture of bioavailable calcium stabilized as amorphous CaCO3 biomineral in crayfish gastroliths. Proc Natl Acad Sci U S A 108(36): 14763-14768.
Hypocalcemia; Section 12: Endocrine and Metabolic Disorders. In: The Merck Manual of Diagnosis and Therapy, 18th edition. Mark H. Beers (Editor-in-Chief), Robert S. Porter (Editor), Thomas V. Jones (Associate Editor), Justin L. Kaplan (Senior Assistant Editor) and Michael Berkwits (Assistant Editor). Merck Research Laboratories, Division of Merck & Co., Inc.; Whitehouse Station, NJ; 2006, pp. 1250-1254. And Merck Manual 18th Edition Japanese Edition, 2006, pp. 1319-1323.
Ihli et al., (2013) Freeze-drying yields stable and pure amorphous calcium carbonate (ACC). Chem Commun 49: 3134-3136.
Kojima et al., (1993) Synthesis of Amorphous Calcium Carbonate and Its Crystallization. Journal of Ceramic Society of Japan 101(10): 1145-1152. Abstract.
Sawada et al., (2003) Adsorption of inorganic phosphates and organic polyphosphonate on calcite. Dalton Trans 2003 (3): 342-347.

AMORPHOUS CALCIUM CARBONATE STABILIZED WITH POLYPHOSPHATES OR BISPHOSPHONATES

FIELD OF THE INVENTION

The present invention provides highly stable compositions comprising amorphous calcium carbonate stabilized by polyphosphates or bisphosphonates, as well as methods of producing, processing, and using same.

BACKGROUND OF THE INVENTION

Calcium is one of the most common and widely dispersed minerals. Calcium is considered as one of the most important minerals in the human body. It is required for maintaining bone mineral density, essential for exocytosis of neurotransmitters, takes part in the contraction of muscle cells, replaces sodium as the depolarizing mineral in the heart, and participates in many other physiological functions. Due to its involvement several medical conditions, calcium is wildly used as a dietary supplement. Calcium supplements are often prepared using calcium carbonate.

Calcium carbonate may be present in several crystalline forms or as amorphous calcium carbonate (ACC). ACC is the less stable form and the most soluble in water. Amorphous calcium carbonate rapidly and completely crystallizes into one of the five more stable polymorphs within minutes in contact with water or even moisture.

In nature, ACC is utilized by a number of organisms, mainly crustaceans and other invertebrates that developed capabilities for stabilizing ACC in transient mineral reservoirs. These organisms require an exceptional efficient mineral source for the periodical mobilization, absorption and precipitation of calcium during molting periods. In some crustaceans, such as the freshwater crayfish, ACC is stored in large quantities in specialized transient storage organs, named the gastrolith, which are developed just prior to the molting event.

In nature, the ACC is stabilized by biological polymers (macromolecules) such as chitin and proteins that prevent the crystallization of the amorphous phase until the triggering of such events. Several publications have showed that crystallization of amorphous calcium carbonate may be prevented or reduced by stabilizing polymers and discrete compounds. WO 2009/053967 discloses that ACC forms a precipitate with phosphorylated peptides that stays stable for at least a month.

WO 2014/024191 discloses a method for preparing ACC stabilized by hydrogen bonding molecules and an organic solvent as stabilizers. It was exemplified that the produced ACC is stable in a suspension for at least 3 hours at about 20° C. when phosphoserine was used as a stabilizer or for at least 10 hour when sucrose was used.

Clarkson et al., *J. Chem. Soc., Faraday Trans.*, 1992, 88, 243-249, reports a study of the spontaneous precipitation of calcium carbonate from aqueous solutions. Clarkson's showed that the presence of few PPM of triphosphate delays the nucleation of crystalline phase of $CaCo_3$.

Sawada, *Pure and Applied Chemistry*, 1997, 69, 921-928 studied the mechanism of the formation and transformation of calcium carbonates polymorphs and their inhibition by phosphorous containing compounds. Sawada showed that EDTMP, an organic tetra-phosphonate comprising two amino group, at high concentration, may prevent transformation between different polymorphs of calcium carbonate. Sawada also asserted that adsorption of EDTMP to calcite is much stronger than that of phosphates, indicating stronger binding and complexation of the EDTMP to Ca atoms than phosphates.

US 2013/0190441 describes stabilized spherical particles of calcium carbonate emphasizing that such particles are suitable as fillers for polymers. The particles may be stabilized by an organic surface active substance. Such particles may be stable in mother liquor for 5 days as has been shown in examples utilizing a phosphonate EDTMP as a stabilizer.

Nebel et al, †*Inorganic Chemistry*, 2008, 47(17) 7874-9 teaches the calcium carbonate phases calcite, aragonite, vaterite, monohydrocalcite (calcium carbonate monohydrate), and ikaite (calcium carbonate hexahydrate) as studied by solid-state NMR spectroscopy ($^1H$ and $^{13}C$).

The reported methods for stabilizing ACC are limited in the stability period of ACC in its amorphous form. In addition, much of the above described methods use organic stabilizers and/or solvents. One technique to enhance the stability of ACC is the preparation of ACC by using an organic solvent such as alcohol, most preferable ethanol.

The presence of such solvents during manufacturing can represent health and safety hazards, increase the cost of the production and post production recovery of the solvents to prevent environmental and safety mishaps. Such solvents or traces thereof are not desired in suspensions used for medical administration and in-vitro media.

Some of the stabilizers that can preserve the stability of ACC in the presence of water or moisture, are unacceptable for animal or human consumption due to their toxicity and adverse effects.

There is a clear and unmet need of novel stable ACC compositions that may be used in the food or pharmaceutical industry as well as highly efficient methods for producing same at commercial scale.

SUMMARY OF THE INVENTION

It has been found according to the present invention that an inorganic polyphosphate or bisphosphonate may stabilize amorphous calcium carbonate for a long period of time, even in an aqueous suspension.

According to one aspect the present invention provides a solid composition comprising amorphous calcium carbonate (ACC), and an inorganic polyphosphate or a pharmaceutically acceptable salt thereof as a stabilizer, wherein the molar ratio between P atoms of the stabilizer and Ca atoms of the ACC (P:Ca molar ratio) is at least about 1:90, and wherein the composition is stable for at least 7 days.

In one embodiment, the composition may have P:Ca molar ratio of about 1:28 to about 1:3 or about 1:25 to about 1:5. In other embodiments the Ca content is about 20 wt % to about 38 wt %, about 30 wt % to about 38% or about 30 wt % to about 36 wt %. Such compositions are stable in solid form for at least 1, 3 or 6 months. In other embodiments such compositions may be stable for 1 or even for 2 years.

In certain embodiments the stabilizer is an inorganic polyphosphate such as triphosphate, hexametaphosphate or pyrophosphate. Such compositions may be characterized by a typical FT-IR spectra and/or DSC thermogram. Such FT-IR spectra have absorption peaks at 865 $cm^{-1}$; and at 1400 $cm^{-1}$ with a shoulder at 1470 $cm^{-1}$ associated with carbonate; and at 1130 $cm^{-1}$ associated with phosphate, and a DSC thermogram comprising an exothermic peak in the range of 365° C. to 550° C.

Any one of the aforementioned compositions may be in the form of a powder.

As provided by the teaching of the present invention, the ACC in the solid composition of the present invention remains stable such that the composition comprises less than 1%, 5%, 10% or 30% of crystalline calcium carbonate out of the total calcium carbonate after storage for a prolonged period of time, e.g., at least 7 days.

The invention also encompasses a composition of the present invention in the form of a suspension further comprising an aqueous carrier. Thus, according to another aspect, the present invention provides a suspension comprising the solid composition of the present invention. According to one embodiment the suspension comprises a solid composition comprising amorphous calcium carbonate (ACC), and an inorganic polyphosphate or a pharmaceutically acceptable salt thereof as a stabilizer, wherein the molar ratio between P atoms of the stabilizer and Ca atoms of the ACC (P:Ca molar ratio) is at least about 1:90, and wherein the solid composition is stable for at least 7 days. In such a suspension, the ACC remains stable for at least a period of time selected from 1, 2, 7, 14 days, 1 and 3 months.

The suspension of the present invention comprises less than about 1%, 5%, 10% or 30% of crystalline calcium carbonate out of the total calcium carbonate.

According to another aspect, the present invention provides a solid composition comprising amorphous calcium carbonate (ACC), and a bisphosphonate or a pharmaceutically acceptable salt thereof as a stabilizer, wherein the molar ratio between P atoms of the stabilizer and Ca atoms of the ACC (P:Ca molar ratio) is at least about 1:90, and wherein the composition comprises more than 5 wt % to about 30 wt % water and is stable for at least 7 days. According to some embodiments the composition comprises more than 10 wt % to about 30 wt % or about 10 wt % to about 20 wt % water.

According to some embodiments the bisphosphonate is etidronic acid, zoledronic acid, medronic acid or alendronic acid.

According to some embodiments the P:Ca molar ratio of about 1:28 to about 1:3 or about 1:25 to about 1:5. In other embodiments the Ca content is about 20 wt % to about 38 wt %, about 30 wt % to about 38% or about 30 wt % to about 36 wt %. Such compositions are stable in solid form for at least 1, 3 or 6 months. In other embodiments such composition may be stable for 1 or even for 2 years.

Any one of the aforementioned compositions may be in the form of a powder.

According to some embodiments, the composition comprises less than about 1%, 5%, 10% or 30% of crystalline calcium carbonate out of the total calcium carbonate.

The invention also encompasses the composition of the present invention in the form of a suspension further comprising an aqueous carrier. Thus, according to a further aspect the presentation invention provides a suspension comprising the solid composition of the present invention. In one embodiments the suspension comprises a solid composition comprising amorphous calcium carbonate (ACC) and a bisphosphonate or a pharmaceutically acceptable salt thereof as a stabilizer, wherein the molar ratio between P atoms of the stabilizer and Ca atoms of the ACC (P:Ca molar ratio) is at least about 1:90, and wherein the solid composition comprises more than 5 wt % to about 30 wt % water and is stable for at least 7 days.

According to one embodiment in such a suspension the ACC remains stable for at least a period time selected from 1, 2, 7, 14 days, 1 or 3 months.

According to one embodiment the suspension comprises less than 1%, 5%, 10% or 30% of crystalline calcium carbonate out of the total calcium carbonate.

The compositions or suspensions of the present invention are devoid of organic solvents. In some embodiments, the compositions or suspensions of the present invention may also comprise one or more organic acids.

The compositions or suspensions of the present invention are formulated for administration to mammal, e.g. human. The composition of the present invention is edible, however it may be also administered by any known acceptable biomedical route of administration.

The invention also discloses that the composition or the suspension of the present invention may be formulated as a pharmaceutical, nutraceutical or cosmetic composition, as a food supplement or a medical food.

According to one aspect the present invention provides a pharmaceutical, nutraceutical or cosmetic composition, a food supplement or a medical food comprising the composition or the suspension of the present invention.

According to some embodiments, any of the pharmaceutical compositions or suspensions according to the present invention are suitable for use in treating a disease or a condition responsive to a calcium carbonate treatment. According to some embodiments the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious disease and dental disease.

In another aspect the present invention provides a method for preparing a composition of the present invention in the form of a suspension, said method comprising mixing aqueous solutions of (i) a calcium source, (ii) the stabilizer and (iii) a carbonate source, to precipitate a stabilized amorphous calcium carbonate, wherein the molar ratio between P atoms of the stabilizer and Ca atoms of the ACC is at least about 1:28.

In a further aspect the present invention provides a method for preparing a composition in the form of a suspension comprising stabilized amorphous calcium carbonate (ACC), comprising the steps of: a) dissolving a calcium source and the stabilizer in water to obtain a solution; b) adding an aqueous solution of a carbonate source to the solution of step (a) to precipitate amorphous calcium carbonate (ACC) so as to obtain an aqueous suspension of ACC; and c) adding an aqueous solution of the stabilizer to the suspension obtained in step (b) to obtain the stabilized ACC suspension, wherein the molar ratio between P atoms of the stabilizer and Ca atoms of the ACC is at least about 1:90.

The method may further comprise filtering the reaction suspension to obtain a cake, drying and milling the cake to obtain a powder. In a preferred embodiment, no organic solvent is added throughout the preparation method. The method also comprises any modifications to said method so as to achieve a composition with a better stability.

According to another aspect the present invention provides a method for treating a disease or a condition responsive to a calcium carbonate treatment, comprising administering an effective amount of a composition of the present invention.

The present invention will be understood and appreciated more fully from the following detailed description taken in conjunction with the appended figures.

DETAILED DESCRIPTION OF THE INVENTION

Figure 1:
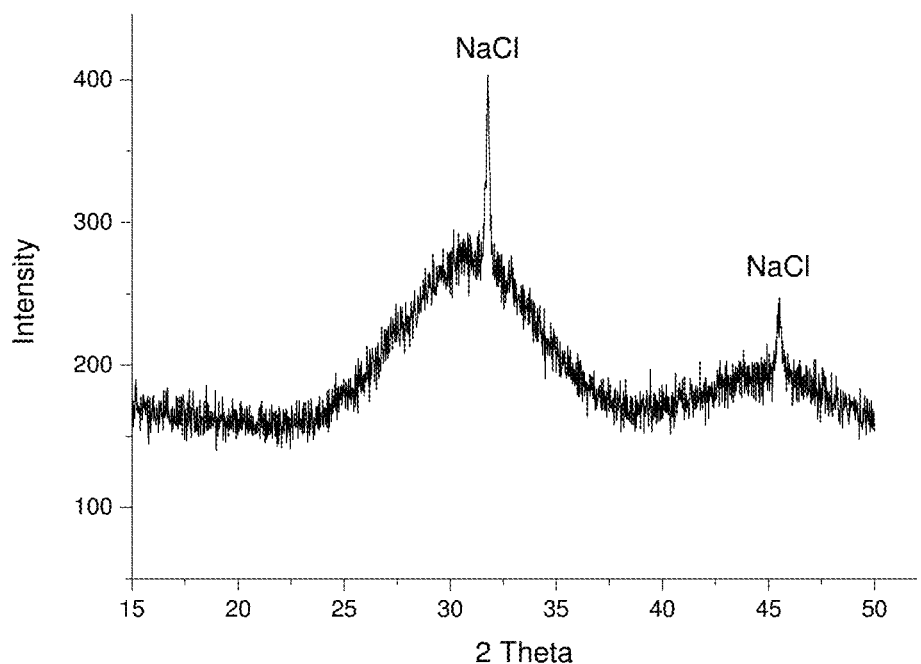
FIG. 1 shows a representative XRD diffractogram of ACC stabilized with 10% triphosphate (composition TP-10%, 100% ACC).

According to one aspect the present invention provides a solid composition comprising amorphous calcium carbonate (ACC), and an inorganic polyphosphate or a pharmaceutically acceptable salt thereof as a stabilizer, wherein the molar ratio between P atoms of the stabilizer and Ca atoms of the ACC (P:Ca molar ratio) is at least about 1:90 and wherein the composition is stable for at least 7 days.

The term "amorphous calcium carbonate" and "ACC" are used herein interchangeably and refers to the non-crystalline form of calcium carbonate. The ACC may contain various levels of adsorbed water and may incorporate small quantities of other elements that form carbonate compositions e.g., sodium carbonate, potassium carbonate, and Magnesium carbonate.

The terms "stabilizer" or "stabilizing agent" as used herein are used interchangeably and refer to any substance that preserves calcium carbonate in the amorphous form during ACC production, formulation and/or storage. In some embodiments the stabilizer is an inorganic polyphosphate or pharmaceutically acceptable salts thereof. In other embodiments the stabilizer is a bisphosphonate or pharmaceutically acceptable salts thereof. In some embodiments the composition may comprise one or more secondary stabilizers. Such secondary stabilizers can be organic compounds known to serve as stabilizers for ACC, e.g., organic compounds containing carboxylic, amine, phosphate, phosphonate and other functional groups that tend to bond, chelate, or complex to Ca atoms such as citric acid, lactate, phosphoserine, gluconate, etc.

The term "inorganic polyphosphate" and "polyphosphate" are used herein interchangeably and refer to an inorganic linear or cyclic chain of phosphate groups linked by phosphoanhydride bonds.

The terms "molar ratio" and "P:Ca molar ratio" refer to a molar ratio between P atoms of the stabilizer and Ca atoms of the ACC. The term greater than and at least 1:90 refers to P:Ca molar ratio of 1 to less than or equal to 90 e.g. 1:80, 1:70, 1:60, 1:50, 1:40, 1:30, 1:20, 1:10, 1:5 etc. as well as and any value in the intervals of these values.

The term "stable" is used herein to indicate that the calcium carbonate is maintained in the amorphous form for a period of time, for example for about at least 7 days in the solid form having less than or about 30% crystalline calcium carbonate According to any one of the above embodiments, the composition is stable for at least 7 days. According to some embodiments, the composition is stable for at least 1 month. According to other embodiments the composition is stable for at least 3 months. According to a further embodiment the composition is stable for 6 months. According to certain embodiments the composition is stable for at least 1 year. According to a particular embodiment, the composition is stable to at least 2 years.

In some embodiments the ACC does not crystallize at all. According to other embodiments some of the ACC converts to a crystalline calcium carbonate. In some embodiments no more than 30% of ACC is converted into the crystalline form and thus the composition comprises less than 30% crystalline calcium carbonate (CCC) of the total calcium carbonate. In certain embodiments, the composition comprises less than 25%, less than 20%, less than 15%, less than 10% or less than 5% of CCC of the total calcium carbonate. The presence of ACC and CCC in the solid composition, as well as their ratio can be measured by any known method. A non-limiting example is X-Ray diffraction (XRD) measurements, as defined in the experimental part.

According to some embodiments, the P:Ca molar ratio is about 1:90 to about 1:1. In one embodiment, the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In another embodiment the P:Ca molar ratio is about 1:28 to about 1:3. In other embodiments, the P:Ca molar ratio is about 1:25 to about 1:4. In further embodiment the P:Ca molar ratio is about 1:20 to about 1:5. In another embodiment the P:Ca molar ratio is about 1:20 to about 1:6. In a particular embodiment, the P:Ca molar ratio is about 1:15 to about 1:5. In another particular embodiment the P:Ca molar ratio is about 1:25 to about 1:5.

According to some embodiments the solid composition of the present invention comprises ACC, wherein the Ca content of the composition is about 1 wt % to about 39 wt % The terms "Ca content" and "calcium content" is used herein interchangeably and refer to the content of calcium of the ACC in the final composition. In other embodiments the Ca content is about 5 wt % to about 38 wt %. In another embodiment, the Ca content is about 10 wt %, about 15 wt %, or about 20 wt % to about 38 wt %. In further embodiments the Ca content is about 25 wt % to about 38 wt %. In further embodiments, the Ca content is about 27 wt % to 38 wt %. In another embodiment the Ca content is about 30 wt % to about 38 wt %. In a particular embodiment the Ca content is about 30 wt % to about 36 wt %.

In certain embodiments the P:Ca molar ratio is about 1:40 to about 1:1, and the Ca content is about 20 wt % to about 38 wt %. In some embodiments the molar ratio is about 1:28 to about 1:3, and the Ca content is about 25 wt % to about 38 wt %. In some embodiments the molar ratio is about 1:28 to about 1:3, and the Ca content is about 30 wt % to about 38 wt %. In another embodiment the molar ratio is 1:25 to about 1:5, and the Ca content is about 30 wt % to about 38 wt %. In yet another embodiment the molar ratio is 1:25 to about 1:5, and the Ca content is about 30 wt % to about 36 wt %.

According to any one of the above embodiments, a solid composition comprises less than 30 wt % water. According to other embodiments, the composition comprises less than 20 wt % water. According to anther embodiments, the composition comprises less than 15 wt % water. According to further embodiments the composition comprises more than 5% water but less than 30 wt % water. According to some embodiments the composition comprises about 5 wt % to about 25 wt % water. According to another embodiment, the composition comprises about 10 wt % to about 20 wt % water. According to further embodiments, the composition comprises about 10 wt % to about 25 wt % water.

According to any one of the above embodiments, the inorganic polyphosphate or a pharmaceutically acceptable salt thereof comprises 2 to 10 phosphate groups, e.g. 2, 3, 4, 5, 6, 7, 8, 9, or 10 phosphate groups. Non-limiting examples of such salt of the polyphosphate are Na, K, Mg, Mn and Zn. According to some embodiments the inorganic polyphosphate is selected from triphosphate, pyrophosphate, and hexametaphosphate. According to another embodiment the stabilizer is triphosphate or pharmaceutically acceptable salts thereof such as sodium triphosphate. The term "triphosphate" and "tripolyphoshate" are used herein interchangeably. According to a further embodiment the stabilizer is hexametaphosphate or pharmaceutically acceptable salts thereof such sodium hexametaphosphate. According to one embodiment the stabilizer is pyrophosphate or pharmaceutically acceptable salts thereof such as sodium pyrophosphate. According to some embodiments, ACC is stabilized by any combination of said stabilizers.

As demonstrated below, the polyphosphate in the composition is stable and does not disintegrate, decompose or break down during formulation or storage.

As exemplified herein, the composition comprising inorganic polyphosphates has a typical FT-IR spectra characterized by several absorption peaks. According to some embodiments the composition is characterized by the FT-IR spectrum having peaks at about 865 cm$^{-1}$; at about 1400 cm$^{-1}$ with a shoulder at about 1470 cm$^{-1}$ associated with carbonate; and at about 1130 cm$^{-1}$ associated with phosphate. The term "about" as used herein in the application with respect to the peaks observed on FT-IR spectrum means ±4 cm$^{-1}$ of than value. According to some embodiments, the composition is characterized by the FT-IR spectrum as shown in FIG. 6, e.g. as shown in FIGS. 6A, 6B, 6C, 6D, 6E 6F, 6G or 6H.

According to some embodiments the composition comprises an inorganic polyphosphate as defined hereinabove, which is characterized by differential scanning calorimetry (DSC) thermograms comprising an exothermic peak associated with crystallization of the ACC in the range of 365° C. to 550° C., wherein the DSC analysis is performed under non-oxidizing conditions with a heating rate of 10° C./min. According to certain embodiments the exothermic peak is in the range of 365° C. to 430° C.

According to some embodiments the stabilizer is an inorganic polyphosphate selected from triphosphate, pyrophosphate, hexametaphosphate and pharmaceutically acceptable salts thereof and the P:Ca molar ratio about 1:40 to about 1:1. In a further embodiment, the P:Ca molar ratio is about 1:35 to about 1:2. In certain embodiments, the P:Ca molar ratio is about 1:30 to about 1:3. In another embodiment the P:Ca molar ratio is about 1:28 to about 1:3. In other embodiment, the P:Ca molar ratio is about 1:25 to about 1:4.

In another particular embodiment the P:Ca molar ratio is about 1:25 to about 1:5. In further embodiments, the Ca content is about 25 wt % to 38 wt %. In another embodiment the Ca content is about 30 wt % to about 38 wt %. In yet another embodiments the Ca content, is about 30 wt % to about 36 wt %. In certain embodiments the P:Ca molar ratio is about 1:40 to about 1:1 and the Ca content is about 25 wt % to about 38 wt %. In some embodiments the molar ratio is 1:28 to about 1:3, and the Ca content is about 30 wt % to about 38 wt %. In another embodiment the molar ratio is 1:25 to about 1:5 and the Ca content is about 30 wt % to about 36 wt %.

According to any one of the above embodiments, the composition is the form of a powder. According to some embodiments the particles of the ACC in the powder have a particle size of less than about 100 µm. In some embodiments, the ACC particles have a particle size of about 100 µm to about 5 µm. In other embodiments, the particle size is about 50 µm to about 5 µm, or about 30 to about 5 µm. In one particular embodiments the particles having the size less than 50 µm, less than 40 µm, less than 30 µm, less than 20 µm or less than 10 µm. According to some embodiments at least 70%, at least 80% or at least 90% of the ACC particles have the particle size of less than 5 µm.

The term "particle" as used herein refers to a discrete microparticle or a nanoparticle of ACC stabilized by the stabilizer as defined hereinabove, as well as to the aggregates or agglomerates thereof. According to some embodiments, the particles are primary particles of the stabilized ACC. The basic nanoparticles are in the range of 5 to 500 nm or 10 to 300 nm or 20 to 100 nm. These nanoparticles immediately agglomerate and aggregate into much larger secondary particles. These aggregation and agglomeration can be then broken by milling and dissolution techniques into smaller particles. According to other embodiments the particles are agglomerates or aggregates of the primary particles, i.e. secondary particles.

In one embodiment the composition is in the form of a powder, the stabilizer is an inorganic polyphosphate selected from triphosphate, pyrophosphate, and hexametaphosphate, and the P:Ca molar ratio of about 1:40 to about 1:1. In a further embodiment, the P:Ca molar ratio is about 1:35 to about 1:2. In certain embodiments, the P:Ca molar ratio is about 1:30 to about 1:3. In another embodiment the P:Ca molar ratio is about 1:28 to about 1:3. In other embodiment, the P:Ca molar ratio is about 1:25 to about 1:4. In another particular embodiment the P:Ca molar ratio is about 1:25 to about 1:5. In another particular embodiment the P:Ca molar ratio is about 1:25 to about 1:5. In further embodiments, the Ca content is about 25 wt % to 38 wt %. In another embodiment the Ca content is about 30 wt % to about 38 wt %. In yet another embodiments the Ca conteint is about 30 wt % to about 36 wt %. In certain embodiments the P:Ca molar ratio is about 1:40 to about 1:1 and the Ca content is 25 wt % to 38 wt %. In some embodiments the molar ratio is 1:28 to about 1:3, and the Ca content is about 30 wt % to about 38 wt %. In another embodiment the molar ratio is 1:25 to about 1:5 and the Ca content is 30 wt % to 36 wt %. Such compositions may be characterized by FT-IR spectrum, DSC thermogram or both FT-IR spectrum and DSC thermogram as defined hereinabove.

According to one embodiment, the invention provides a suspension comprising the solid composition of the present invention according to any of the embodiments described herein.

According to some embodiments, the invention provides a composition in the form of a suspension comprising the composition according to any one of the above embodiments and an aqueous carrier. The term "aqueous carrier" as used herein refers to the aqueous vehicle in which the ACC is administered, dispersed, and/or suspended. Non-limiting examples of aqueous carriers include water and water based solutions (e.g. saline).

According to some embodiments the composition in the form of a suspension comprises a solid composition comprising ACC and an inorganic polyphosphate or a pharmaceutically acceptable salt thereof as a stabilizer, wherein the P:Ca molar ratio is at least about 1:90, in an aqueous carrier. According to some embodiments the P:Ca molar ratio of about 1:40 to about 1:1. In a further embodiment, the P:Ca molar ratio is about 1:35 to about 1:2. In certain embodiments, the P:Ca molar ratio is about 1:30 to about 1:3. In another embodiment the P:Ca molar ratio is about 1:28 to about 1:3. In other embodiment, the P:Ca molar ratio is about 1:25 to about 1:4. In another particular embodiment the P:Ca molar ratio is about 1:25 to about 1:5. Such compositions may have the Ca content of about 25 wt % to 38 wt %. In another embodiment the Ca content is about 30 wt % to about 38 wt %. In yet another embodiments the Ca content, is about 30 wt % to about 36 wt %. In certain embodiments the P:Ca molar ratio is about 1:40 to about 1:1 and the Ca content is about 25 wt % to about 38 wt %. In some embodiments the molar ratio is 1:28 to about 1:3, and the Ca content is about 30 wt % to about 38 wt %. In another embodiment the molar ratio is 1:25 to about 1:5 and the Ca content is about 30 wt % to about 36 wt %. According to certain embodiments the solid composition is characterized by the FT-IR spectrum having peaks at about 865 cm$^{-1}$; at about 1400 cm$^{-1}$ with a shoulder at about 1470 cm$^{-1}$ associated with a carbonate; and at about 1130 cm$^{-1}$ associated with phosphate. In other embodiments such solid compositions is characterized by a DSC thermogram comprising an exothermic peak associated with crystallization of the ACC in the range of 365° C. to 550° C., wherein the DSC analysis is performed under non-oxidizing conditions with a heating rate of 10° C./min. In a further embodiments such composition is characterized by both FT-IR spectrum and DSC thermogram as defined hereinabove.

According to some embodiments the ACC in the composition in the form of a suspension remains stable for at least 1 day. According to some embodiments the ACC in the composition in the form of a suspension remains stable for 2 days. According to a further embodiment, the ACC in the composition in the form of a suspension remains stable for 7 days. According to yet another embodiment, the ACC in the composition in the form of a suspension remains stable for 14 days. According to other embodiments the ACC in the composition in the form of a suspension remains stable for at least 1 month. According to further embodiments the ACC in the composition in the form of a suspension remains stable for at least 3 months. According to one embodiment, the ACC remains stable for at least a time period selected from 1, 2, 7, 14 days, 1 and 3 months.

As defined above the composition of the present invention, e.g. the solid composition or the composition in the form of a suspension is stable. According to any one of the above embodiments the composition comprises less than 1%, 5%, 10% or 30% of crystalline calcium carbonate out of the total calcium carbonate. According to other embodiments the composition comprises less than 5% CCC. According to a further embodiment the composition comprises less than 10% CCC. According to other embodiments the composition comprises less than 15% CCC. According to yet another embodiment the composition comprises less than 20% CCC. In other embodiments the composition comprises less than 25% or less than 30% CCC out of the total calcium carbonate.

According to any one of the above embodiments the composition according to the present invention, i.e. the solid composition or the composition in the form of a suspension is devoid of organic solvents. The term "devoid" as used herein refers to a composition, which does not comprise a detectable amount of organic solvent. In a preferred embodiment the entire processing and suspension do not involve any organic solvent incorporation and subsequently the ACC does not comprise any organic solvent. Organic solvents referred are those used in food and drug processing. Such organic solvents are polar and water soluble or miscible. In some embodiments such organic solvent may be ethanol or acetone. Thus in one embodiments the composition of the present invention is devoid of ethanol.

According to any one of the above embodiments the composition according to the present invention, i.e. the solid composition or the composition in the form of a suspension, further comprises one or more organic acids.

According to some embodiments the organic acid is selected from the group consisting of citric acid, tartaric acid, malic acid, ascorbic acid, lactic acid, acetic acid, oxalic acid, malonic acid, glutaconic acid, succinic acid, maleic acid, lactic acid, and aconitic acid.

According to any one of the above embodiments, the composition of the present invention may comprise one or more secondary stabilizers. The secondary stabilizer may be an inorganic or organic compound containing functional groups capable of bonding or chelating to Ca atoms. The secondary stabilizer may in some embodiments be present in a lower amount than the first stabilizer. In some embodiments such secondary stabilizer does not by itself provide the stability as defined hereinabove. In other embodiments the secondary stabilizer is identical to the first stabilizer. In some embodiments the secondary stabilizer is an organic compounds containing functional groups such as carboxylic acids, amines, hydroxyl, phosphates or phosphonates, which are capable of strong bonding to Ca atoms.

According to any one of the above embodiments the composition is formulated for administration to a mammal. The term "mammal" refers to human and non-human mammals. In one embodiment the mammal is a human. In another embodiment the mammal is a non-human mammal selected from cattle, pigs, sheep, goats, horses, mules, donkeys, buffalo, or camels.

According to any one of the above embodiments, the composition is edible.

According to a certain embodiments, the solid composition comprising ACC stabilized by triphosphate, pyrophosphate, or hexametaphosphate, has the P:Ca molar ratio of about 1:28 to about 1:3, comprises about 10 wt % to about 25 wt % water and is stable for at least 1 month. In certain embodiment, the P:Ca molar ratio is about 1:25 to about 1:4. According to certain embodiment the P:Ca molar ratio is about 1:25 to about 1:5. In further embodiments, the Ca content is about 25 wt % to 38 wt %. In another embodiment the Ca content is about 30 wt % to about 38 wt %. In yet another embodiment the Ca content, is about 30 wt % to about 36 wt %. In certain embodiments the P:Ca molar ratio is about 1:40 to about 1:1 and the Ca content is 25 wt % to 38 wt %. In another embodiment the molar ratio is 1:25 to about 1:5 and the Ca content is 30 wt % to 36 wt %. According to some embodiments the composition is stable for at least 3 months. According to other embodiments the composition is stable for 6 months. According to a further embodiment the composition is stable 1 year. According to another embodiment the composition comprises less than 20% or less than 10% of crystalline calcium carbonate out of the total calcium carbonate. According to some embodiments the composition is in the form of a powder. According to some embodiments the composition is devoid of organic solvents. According to some embodiments, such a composition is characterized by the FT-IR spectrum having peaks at about 865 cm$^{-1}$; at about 1400 cm$^{-1}$ with a shoulder at about 1470 cm$^{-1}$ associated with a carbonate; and at about 1130 cm$^{-1}$ associated with phosphate. In other embodiments such compositions is characterized by a DSC thermogram comprising an exothermic peak associated with crystallization of the ACC in the range of 365° C. to 550° C., wherein the DSC analysis is performed under non-oxidizing conditions with a heating rate of 10° C./min. In a further embodiments such composition may be characterized by both FT-IR spectrum and DSC thermogram as defined hereinabove.

According to one embodiment the solid composition ACC stabilized by triphosphate, e.g. sodium triphosphate, wherein the P:Ca molar ratio of about 1:25 to about 1:5, the composition comprises about 10 wt % to about 25 wt % water and is stable for at least 7 days, comprises less than 30% of crystalline calcium carbonate out of the total calcium carbonate and devoid of organic solvents. According to another embodiment the solid composition comprising ACC stabilized by hexametaphosphate, e.g. sodium hexametaphosphate, wherein the P:Ca molar ratio of about 1:25 to about 1:5, the composition comprises about 10 wt % to about 25 wt % water and is stable for at least 1 month, comprises less than 30% of crystalline calcium carbonate out of the total calcium carbonate and devoid of organic solvents. According to a further embodiment the solid composition of the present invention comprising amorphous calcium (ACC) stabilized by pyrophosphate, e.g. sodium pyrophosphate, wherein the P:Ca molar ratio of about 1:25 to about 1:5, the composition comprises about 10 wt % to about 25 wt % water and is stable for at least 1 month, comprises less than 30% of crystalline calcium carbonate out of the total calcium carbonate and devoid of organic solvents. According to any one of the above embodiments such compositions have the Ca content of about 30 wt % to about 38 wt %. In some embodiments the molar ratio is 1:25 to about 1:5, and the Ca content is about 30 wt % to about 36 wt %. According to some embodiments the composition is stable for at least 3 months. According to other embodiments the composition is stable for 6 months. According to a further embodiment the composition is stable 1 year. According to another embodiment the composition comprises less than 20% or less than 10% of crystalline calcium carbonate out of the total calcium carbonate. According to some embodiments the composition is in the form of a powder. Such a composition may be characterized may be characterized by the FT-IR spectrum having peaks at about 865 cm$^{-1}$; at about 1400 cm$^{-1}$ with a shoulder at about 1470 cm$^{-1}$ associated with carbonate; and at about 1130 cm$^{-1}$ associated with phosphate. In other embodiments such compositions may be characterized by a DSC thermogram comprising an exothermic peak associated with crystallization of the ACC in the range of 365° C. to 550° C., wherein the DSC analysis is performed under non-oxidizing conditions with a heating rate of 10° C./min. In a further embodiments such composition may be characterized by both FT-IR spectrum and DSC thermogram as defined hereinabove. According to some embodiments such composition further comprise an organic acid as defined hereinabove. According to some embodiments the composition is characterized by an FT-IR spectrum as shown in FIG. 6, e.g. as shown in FIG. 6A, 6B, 6C, 6D, 6E, 6E, 6F, 6G or 6H.

According to one embodiment the solid composition of the present invention comprising ACC stabilized by triphosphate, e.g. sodium triphosphate, wherein the P:Ca molar ratio of about 1:25 to about 1:5, the composition comprises about 10 wt % to about 25 wt % water has Ca content of about 30 wt % to about 38 wt %, stable for at least 1 month, comprises less than 20% of crystalline calcium carbonate out of the total calcium carbonate and devoid of organic solvents. According to another embodiment the solid composition of the present invention comprising ACC stabilized by hexametaphosphate, e.g. sodium hexametaphosphate, wherein the P:Ca molar ratio of about 1:25 to about 1:5, the composition comprises about 10 wt % to about 25 wt % water has Ca content of about 30 wt % to about 38 wt %, stable for at least 1 month, comprises less than 20% of crystalline calcium carbonate out of the total calcium carbonate and devoid of organic solvents. According to a further embodiment the solid composition of the present invention comprising ACC stabilized by pyrophosphate, e.g. sodium pyrophosphate, wherein the P:Ca molar ratio of about 1:25 to about 1:5, the composition comprises about 10 wt % to about 25 wt % water has Ca content of about 30 wt % to about 38 wt %, stable for at least 1 month, comprises less than 20% of crystalline calcium carbonate out of the total calcium carbonate and devoid of organic solvents. According to any of the above embodiments composition is in the form of a powder. According to some embodiments the composition is characterized by the FT-IR spectrum having peaks at about 865 cm$^{-1}$; at about 1400 cm$^{-1}$ with a shoulder at about 1470 cm$^{-1}$ associated with carbonate; and at about 1130 cm$^{-1}$ associated with phosphate. In other embodiments such compositions may be characterized by a DSC thermogram comprising an exothermic peak associated with crystallization of the ACC in the range of 365° C. to 550° C., wherein the DSC analysis is performed under non-oxidizing conditions with a heating rate of 10° C./min. In a further embodiments such composition is characterized by both FT-IR spectrum and DSC thermogram as defined hereinabove. According to some embodiments such composition further comprise an organic acid as defined hereinabove. In some embodiments the molar ratio is 1:25 to about 1:5, and the Ca content is about 30 wt % to about 36 wt %. According to some embodiments the composition is stable for at least 3 months. According to other embodiments the composition is stable for 6 months. According to a further embodiment the composition is stable 1 year. According to another embodiment the composition comprises less than 10% of crystalline calcium carbonate out of the total calcium carbonate. According to some embodiments the composition is characterized by an FT-IR spectrum as shown in FIG. 6, e.g. as shown in FIG. 6A, 6B, 6C, 6D, 6E, 6E, 6F, 6G or 6H.

According to certain embodiments, the composition according to any one of the above embodiments is formulated as a pharmaceutical, nutraceutical or cosmetic composition, as a food supplement or a medical food. According to one embodiment the composition is formulated as a pharmaceutical composition. According to another embodiment the composition is formulated as a nutraceutical composition. According to a further embodiment the composition is formulated as a food supplements. According to yet another embodiment the composition is formulated as a medical food.

The term "pharmaceutical composition" as used herein refers to a composition comprising stabilized ACC as disclosed herein as an active agent, formulated together with one or more pharmaceutically acceptable carriers.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, and the like, that are compatible with pharmaceutical administration. The use of such media and agents for pharmaceutically active substances is well known in the art. The compositions may contain other active compounds providing supplemental, additional, or enhanced therapeutic functions.

The terms "pharmaceutically acceptable" and "pharmacologically acceptable" include molecular entities and compositions that do not produce an adverse, allergic, or other untoward reactions when administered to an animal, or human, as appropriate.

As used herein, the term "nutraceutical composition" refers to a composition suitable for use in human beings or animals, comprising one or more natural products with therapeutic action which provide a health benefit or have been associated with disease prevention or reduction.

The term "food supplement" is used to mean a product containing said composition and intended to supplement the food by providing nutrients that are beneficial to health according to any acceptable directive, such as European directive. For example, a food supplement may be a capsule or a tablet for swallowing, or a powder or small vial to mix with a food and providing beneficial health effects.

The term "cosmetic composition" as used herein e.g. refers to topical compositions for care of the human skin.

As used herein, the term "medical food" refers to a food item specially formulated for the dietary management of a disease or disorder in a subject.

In one embodiment the present invention provides a food supplement comprising the composition as defined in any one of the above embodiments. In other embodiment the present invention provides a pharmaceutical composition comprising the composition as defined in any one of the above embodiments. In one embodiment the pharmaceutical composition or the food supplement comprises a solid composition comprising ACC, and an inorganic polyphosphate or a pharmaceutically acceptable salts thereof as a stabilizer, wherein P:Ca molar ratio at least about 1:90, and the composition is stable for at least 7 days. In one embodiment, the P:Ca molar ratio is about 1:40 to about 1:1. In further embodiment, the P:Ca molar ratio is about 1:35 to about 1:2. In certain embodiments, the P:Ca molar ratio is about 1:30 to about 1:3. In another embodiment the P:Ca molar ratio is about 1:28 to about 1:3. In other embodiment, the P:Ca molar ratio is about 1:25 to about 1:4. In another particular embodiment the P:Ca molar ratio is about 1:25 to about 1:5. In some embodiments, the Ca content is about 25 wt % to 38 wt %. In another embodiment the Ca content is about 30 wt % to about 38 wt %. In yet another embodiment the Ca content, is about 30 wt % to about 36 wt %. In certain embodiments the P:Ca molar ratio is about 1:40 to about 1:1 and the Ca content is about 25 wt % to about 38 wt %. In some embodiments the molar ratio is 1:28 to about 1:3, and the Ca content is about 30 wt % to about 38 wt %. In another embodiment the molar ratio is 1:25 to about 1:5 and the Ca content is about 30 wt % to about 36 wt %. According to some embodiments, the solid composition comprises less than 30 wt % water. According to other embodiments, the composition comprises less than 20 wt % water. According to certain embodiments, the composition comprising 5 wt % to about 30 wt % water. According to another embodiment the composition comprising 5 wt % to about 25 wt % water. According to other embodiment, the solid composition comprises about 10 wt % to about 20 wt % water. According to further embodiments, the solid composition comprises about 10 wt % to about 20 wt % water. According to some embodiments the inorganic polyphosphate is selected from pyrophosphate, triphosphate, and hexametaphosphate. According to one embodiment the stabilizer is pyrophosphate or pharmaceutically acceptable salts thereof such as sodium pyrophosphate. According to another embodiment the stabilizer is triphosphate or pharmaceutically acceptable salts thereof such as sodium triphosphate. According to a further embodiment the stabilizer is hexametaphosphate or pharmaceutically acceptable salts thereof such sodium hexametaphosphate. According to certain embodiments such a solid composition is characterized by the FT-IR spectrum having peaks at about 865 $cm^{-1}$; at about 1400 $cm^{-1}$ with a shoulder at about 1470 $cm^{-1}$ associated with carbonate; and at about 1130 $cm^{-1}$ associated with phosphate. In other embodiments such compositions may be characterized by a DSC thermogram comprising an exothermic peak associated with crystallization of the ACC in the range of 365° C. to 550° C., wherein the DSC analysis is performed under non-oxidizing conditions with a heating rate of 10° C./min. In a further embodiments such composition may be characterized by both FT-IR spectrum and DSC thermogram as defined hereinabove. According to one embodiment, the composition is the form of a powder. According to another embodiment, the solid composition comprises less than 1%, 5%, 10% or 30% of crystalline calcium carbonate out of the total calcium carbonate. According to some embodiments the composition is devoid of organic solvents.

According to some other embodiments the pharmaceutical or food supplement comprises the composition of the present invention in the form of a suspension as defined hereinabove. As defined, such suspension composition comprises a solid composition according to the present invention.

According to some embodiments the pharmaceutical composition or the food supplement comprises the solid composition comprising ACC stabilized by triphosphate, e.g. sodium triphosphate, wherein the P:Ca molar ratio of about 1:25 to about 1:5, the composition comprises about 10 wt % to about 25 wt % water and is stable for at least 1 month, comprises less than 30% of crystalline calcium carbonate out of the total calcium carbonate and devoid of organic solvents. According to another embodiments the solid composition comprising ACC stabilized by hexametaphosphate, e.g. sodium hexametaphosphate, wherein the P:Ca molar ratio of about 1:25 to about 1:5, the composition comprises about 10 wt % to about 25 wt % water, comprises less than 30% of crystalline calcium carbonate out of the total calcium carbonate and devoid of organic solvents. In a further embodiment the solid composition comprising ACC stabilized by pyrophosphate, e.g. sodium pyrophosphate, wherein the P:Ca molar ratio of about 1:25 to about 1:5, the composition comprises about 10 wt % to about 25 wt % water, comprises less than 30% of crystalline calcium carbonate out of the total calcium carbonate and devoid of organic solvents. In further embodiments such composition has the Ca content of about 30 wt % to about 38 wt %. In some embodiments the molar ratio is 1:25 to about 1:5, and the Ca content is about 30 wt % to about 38 wt %. According to some embodiments the composition such a composition is characterized by the FT-IR spectrum having peaks at about 865 $cm^{-1}$; at about 1400 $cm^{-1}$ with a shoulder at about 1470 $cm^{-1}$ associated with carbonate; and at about 1130 $cm^{-1}$ associated with phosphate. In other embodiments such compositions is characterized by a DSC thermogram comprising an exothermic peak associated with crystallization of the ACC in the range of 365° C. to 550° C., wherein the DSC analysis is performed under non-oxidizing conditions with a heating rate of 10° C./min. In a further embodiments such composition may be characterized by both FT-IR spectrum and DSC thermogram as defined hereinabove.

The pharmaceutical, nutraceutical or cosmetic composition, the food supplement or the medical food according to any one of the above embodiments may be prepared in any known administrable form. Non-limiting examples for such preparations are tablets, troches, lozenges, aqueous, or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations.

According to certain embodiments the pharmaceutical, nutraceutical or cosmetic composition, the food supplement or the medical food according to any one of the above embodiments is formulated as a tablet, capsule, microencapsulated pellets, powder, suspension, ointment, and functional food, a formulation for buccal administration or for administration via inhalation.

According to some embodiments, the pharmaceutical composition according to the present invention is for use in treating a disease or a condition responsive to a calcium carbonate treatment. According to some embodiments the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious disease and dental disease. According to one particular embodiment, the disease is cancer.

According to some embodiments the present invention provides use of a composition according to any one of the above embodiments for preparing a medicament for treating a disease or a condition responsive to a calcium carbonate treatment. According to some embodiments the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious disease and dental disease. According to one particular embodiment, the disease is cancer.

According to another aspect, the present invention provides a solid composition comprising amorphous calcium carbonate (ACC), and a bisphosphonate or a pharmaceutically acceptable salt thereof as a stabilizer, wherein the molar ratio between P atoms of the stabilizer and Ca atoms of the ACC (P:Ca molar ratio) is at least about 1:90, and wherein the composition comprises more than 5 wt % to about 30 wt % water and is stable for at least 7 days.

According to some embodiments, the P:Ca molar ratio is about 1:90 to about 1:1. In one embodiment, the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In another embodiment the P:Ca molar ratio is about 1:28 to about 1:3. In other embodiments, the P:Ca molar ratio is about 1:25 to about 1:4. In further embodiment the P:Ca molar ratio is about 1:20 to about 1:5. In another embodiment the P:Ca molar ratio is about 1:20 to about 1:6. In a particular embodiment, the P:Ca molar ratio is about 1:15 to about 1:5. In another particular embodiment the P:Ca molar ratio is about 1:25 to about 1:5.

In one embodiments the solid composition of the present invention comprises ACC, wherein the Ca content is about 1 wt % to about 39 wt %. In other embodiments, the Ca content is about 5 wt % to about 38 wt %. In another embodiment, the Ca content is about 10 wt %, about 15 wt %, or about 20 wt % to about 38 wt %. In further embodiments, the Ca content is about 25 wt % to about 38 wt %. In further embodiments, the Ca content is about 27 wt % to 38 wt %. In another embodiment the Ca content is about 30 wt % to about 38 wt %. In a particular embodiment the Ca content is about 30 wt % to about 36 wt %.

In certain embodiments the P:Ca molar ratio is about 1:40 to about 1:1, and the Ca content is about 25 wt % to about 38 wt %. In some embodiments the molar ratio is about 1:28 to about 1:3, and the Ca content is about 27 wt % to about 38 wt %. In some embodiments the molar ratio is about 1:28 to about 1:3, and the Ca content is about 30 wt % to about 38 wt %. In another embodiment the molar ratio is 1:25 to about 1:5, and the Ca content is about 30 wt % to about 38 wt %. In yet another embodiment the molar ratio is 1:25 to about 1:5, and the Ca content is about 30 wt % to about 36 wt %.

The term "bisphosphonate" refers to a compound with two $PO_3$ (phosphonate) groups covalently linked to a carbon.

According to some embodiments the bisphosphonate is selected from the group consisting of etidronic acid, zoledronic acid, medronic acid, alendronic acid and pharmaceutically acceptable salts thereof. non-limiting examples of bisphosphonate salt are Na, K, Mg, Mn and Zn.

According to some embodiments the stabilizer is an etidronic acid or pharmaceutically acceptable salts thereof. According to another embodiment the stabilizer is a zoledronic acid or pharmaceutically acceptable salts thereof. According to a further embodiment the stabilizer is a medronic acid or pharmaceutically acceptable salts thereof. According to certain embodiments the stabilizer is alendronic acid or pharmaceutically acceptable salts thereof.

According to any one of the above embodiments, the composition of the present invention may comprise one or more secondary stabilizers as defined hereinabove. A secondary stabilizer may be an inorganic or organic compound containing functional groups capable of bonding or chelating to Ca atoms. The secondary stabilizer may in some embodiments be present in a lower amount than the first stabilizer. In some embodiments such secondary stabilizer does not by itself provide the stability as defined hereinabove. In other embodiments the secondary stabilizer is identical to the first stabilizer.

In some embodiments the secondary stabilizer is an organic compounds containing functional groups such as carboxylic acids, amines, hydroxyl, phosphates or phosphonates, which are capable of strong bonding to Ca atoms According to any one of the above embodiments, a solid composition comprises more than 5% water but less than 30 wt % water. According to one embodiment the composition comprises more than 10% water but less than 30 wt % water. According to some embodiments the composition comprises more than 5 wt % to about 25 wt % water. According to another embodiment, the composition comprises about 10 wt % to about 20 wt % water. According to further embodiments, the composition comprises about 10 wt % to about 25 wt % water.

The composition according to the present invention is stable for a long period of time. According to some embodiments, the composition is stable for at least 1 month. According to other embodiments the composition is stable for at least 3 months. According to a further embodiment the composition is stable for 6 months. According to certain embodiment the composition is stable for at least 1 year. According to a particular embodiment, the composition is stable to at least 2 years.

In some embodiments no more than 30% of ACC is converted into the crystalline form and thus the composition comprises less than 30% crystalline calcium carbonate (CCC) of the total calcium carbonate. In certain embodiments, the composition comprises less than 25%, less than 20%, less than 15%, less than 10% or less than 5% of CCC of the total calcium carbonate.

According to any one of the above embodiments, the composition is the form of a powder. According to some embodiments the particles of the ACC in the powder has a particle size of less than about 100 µm. In some embodiments the ACC particles have a particle size of about 100 µm to about 5 µm. In other embodiments, the particle size is about 50 µm to about 5 µm, or about 30 to about 5 µm. In one particular embodiments the particles having the size less than 50 µm, less than 40 µm, less than 30 µm, less than 20 µm or less than 10 µm. According to some embodiments at least 70%, at least 80% or at least 90% of the ACC particles have the particle size of less than 5 µm.

According to another embodiment the composition is in the form of a powder, the stabilizer is selected from etidronic acid, zoledronic acid, medronic acid, alendronic acid and pharmaceutically acceptable salts thereof, and the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In another embodiment the P:Ca molar ratio is about 1:28 to about 1:3. In other embodiment, the P:Ca molar ratio is about 1:25 to about 1:4. In another particular embodiment the P:Ca molar ratio is about 1:25 to about 1:5. In another particular embodiment the P:Ca molar ratio is about 1:25 to about 1:5. In further embodiments, the Ca content is about 25 wt % to 38 wt %. In another embodiment the Ca content is about 30 wt % to about 38 wt %. In yet another embodiment the Ca content is about 30 wt % to about 36 wt %. In certain embodiments the P:Ca molar ratio is about 1:40 to about 1:1 and the Ca content is 25 wt % to 38 wt %. In some embodiments the molar ratio is 1:28 to about 1:3, and the Ca content is about 30 wt % to about 38 wt %. In another embodiment the molar ratio is 1:25 to about 1:5 and the Ca content is 30 wt % to 36 wt %. According to some embodiments, the composition comprises more than 5 wt % or more than 10 wt % to about 30 wt % water. In certain embodiments, the composition comprises less than 25%, less than 20%, less than 15%, less than 10% or less than 5% of CCC of the total calcium carbonate.

According to one embodiment, the invention provides a suspension comprising the solid composition of the present invention. According to certain embodiments, the solid composition is according to any one of the above embodiments.

According to one embodiment the invention provides a composition in the form of a suspension comprising the composition according to any one of the above embodiments and an aqueous carrier.

According to some embodiments the ACC in the composition in the form of a suspension remains stable for at least 1 day. According to some embodiments the ACC in the composition in the form of a suspension remains stable for 2 day. According to a further embodiment, the ACC in the composition in the form of a suspension remains stable for 7 days. According to yet another embodiment, the ACC in the composition in the form of a suspension remains stable for 14 days. According to other embodiments the ACC in the composition in the form of a suspension remains stable for at least 1 month. According to further embodiments the ACC in the composition in the form of a suspension remains stable for at least 3 months. According to one embodiment the ACC remains stable for at least a time period selected from 1, 2, 7, 14 days, 1 and 3 months.

As defined above the composition of the present invention is stable. According to any one of the above embodiments the composition comprises less than 1%, 5%, 10% or 30% of crystalline calcium carbonate out of the total calcium carbonate. According to other embodiments the composition comprises less than 5% CCC. According to a further embodiment the composition comprises less than 10% CCC. According to other embodiments the composition comprises less than 15% CCC. According to yet another embodiment the composition comprises less than 20% CCC. In other embodiments the composition comprises less than 25% or less than 30% CCC out of the total calcium carbonate.

According to some embodiments the composition is devoid of organic solvents.

According to any one of the above embodiments the composition according to the present invention, i.e. the solid composition or the composition in the form of a suspension, further comprises one or more organic acids as defined hereinabove.

According to any one of the above embodiments, the composition of the present invention e.g. a suspension, may comprise a secondary stabilizer as defined hereinabove.

According to any one of the above embodiments, the composition is edible.

According to certain embodiments, the composition according to any one of the above embodiments is formulated as a pharmaceutical, nutraceutical or cosmetic composition, as a food supplement or a medical food. According to one embodiment the composition is formulated as a pharmaceutical composition.

In one embodiment the present invention provides a food supplement comprising the composition as defined in any one of the above embodiments. In other embodiment the present invention provides a pharmaceutical composition comprising the composition as defined any one of the above embodiments. In one embodiment the composition is a solid composition comprising ACC and a bisphosphonate such as etidronic acid, zoledronic acid, medronic acid, alendronic acid and pharmaceutically acceptable salts thereof as a stabilizer, wherein P:Ca molar ratio at least about 1:90, and wherein the composition comprises more than 5 wt % to about 30 wt % water and is stable for at least 7 days. In one embodiment, the P:Ca molar ratio is about 1:40 to about 1:1. In further embodiment, the P:Ca molar ratio is about 1:35 to about 1:2. In certain embodiments, the P:Ca molar ratio is about 1:30 to about 1:3. In another embodiment the P:Ca molar ratio is about 1:28 to about 1:3. In other embodiment, the P:Ca molar ratio is about 1:25 to about 1:4. In another particular embodiment the P:Ca molar ratio is about 1:25 to about 1:5. In some embodiments, the Ca content is about 25 wt % to about 38 wt %. In another embodiment the Ca content is about 30 wt % to about 38 wt %. In yet another embodiment the Ca content, is about 30 wt % to about 36 wt %. In certain embodiments the P:Ca molar ratio is about 1:40 to about 1:1 and the Ca content is about 25 wt % to about 38 wt %. In some embodiments the molar ratio is about 1:28 to about 1:3, and the Ca content is about 30 wt % to about 38 wt %. In another embodiment the molar ratio is about 1:25 to about 1:5 and the Ca content is 30 wt % to 36 wt %. According to some embodiments, the solid composition comprises more than 5 wt % to about 25 wt % water. According to other embodiment, the solid composition comprises about 10 wt % to about 20 wt % water. According to further embodiments, the solid composition comprises about 10 wt % to about 20 wt % water. According to any one of the above embodiments the solid composition comprises less than 1%, 5%, 10% or 30% of crystalline calcium carbonate out of the total calcium carbonate. According to some embodiments the composition is devoid of organic solvents. According to another embodiment, the composition further comprising an organic acid.

According to some other embodiments the pharmaceutical or food supplement comprises the composition of the present invention in the form of a suspension as defined hereinabove. As defined, such suspension composition comprises a solid composition according to the present invention.

According to certain embodiments the pharmaceutical, nutraceutical or cosmetic composition, the food supplement or the medical food according to any one of the above embodiments is formulated as a tablet, capsule, microencapsulated pellets, powder, suspension, ointment, and functional food, a formulation for buccal administration or for administration via inhalation.

According to some embodiments, the pharmaceutical composition according to the present invention is for use in treating a disease or a condition responsive to a calcium carbonate treatment. According to some embodiments the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious disease and dental disease. According to one particular embodiment, the disease is cancer.

According to certain aspects, the present invention provides a solid composition comprising amorphous calcium carbonate (ACC) stabilized by a stabilizer selected from the group consisting of an inorganic polyphosphate, a bisphosphonate, and pharmaceutically acceptable salts thereof, wherein the molar ratio between P atoms of the stabilizer and Ca atoms of the ACC (P:Ca molar ratio) is at least about 1:90, and the composition is stable for at least 7 days.

According to another aspect the present invention provides a method of preparing a composition in the form of a suspension comprising stabilized amorphous calcium carbonate (ACC), and an inorganic polyphosphate, a bisphosphonate or a pharmaceutically acceptable salt thereof as a stabilizer, comprising mixing aqueous solutions of: (i) a calcium source, (ii) the stabilizer, and (iii) a carbonate source, to precipitate a stabilized amorphous calcium carbonate, wherein the molar ratio between P atoms of the stabilizer and Ca atoms of the ACC is at least about 1:28.

In a further aspect the present invention provides a method for preparing a composition in the form of a suspension comprising stabilized amorphous calcium carbonate (ACC), comprising the steps of:
a) dissolving a calcium source and the stabilizer in water to obtain a solution;
b) adding an aqueous solution of a carbonate source to the solution of step (a) to precipitate amorphous calcium carbonate (ACC) so as to obtain an aqueous suspension of ACC; and
c) adding an aqueous solution of the stabilizer to the suspension obtained in step (b) to obtain the stabilized ACC suspension,
wherein the molar ratio between P atoms of the stabilizer and Ca atoms of the ACC is at least about 1:90.

The term "aqueous solution" as used herein refers to any water based solution, that has the ability to dissolve all or part of the above mentioned sources at ambient temperature.

According to some embodiments the stabilizer is as defined hereinabove. According to some embodiments the stabilizer is an inorganic polyphosphate or pharmaceutically acceptable salts thereof as defined hereinabove. According to another embodiments the stabilizer is a bisphosphonate as defined hereinabove.

According to a certain aspect, the method of preparing a composition of the present invention comprising the steps of:
a) dissolving a calcium source and an inorganic polyphosphate in water to obtain a solution;
b) adding an aqueous solution of a carbonate source to the solution of step (a) to precipitate amorphous calcium carbonate (ACC) so as to obtain an aqueous suspension of ACC; and
c) adding an aqueous solution of an inorganic polyphosphate to the suspension obtained in step (b) to obtain the stabilized ACC suspension,
wherein the molar ratio between P atoms of the stabilizer and Ca atoms of the ACC is at least about 1:90.

According to some embodiments the method comprises adding one stabilizer during the precipitation of the ACC and adding a second stabilizer after the precipitation of the ACC. The first and the second-step stabilizers can be the same or different stabilizers according to the present invention.

According to some embodiments the inorganic polyphosphate is as defined above. In one particular embodiment the polyphosphate comprises 2 to 10 phosphate groups. According to another embodiments the inorganic polyphosphate is selected from the group consisting of pyrophosphate, triphosphate, hexametaphosphate, and pharmaceutically acceptable salts thereof.

According to some embodiments the P:Ca molar ratio is about 1:40 to about 1:1, or about 1:25 to about 1:5. In a further embodiment, the P:Ca molar ratio is about 1:35 to about 1:2. In certain embodiments, the P:Ca molar ratio is about 1:30 to about 1:3. In another embodiment the P:Ca molar ratio is about 1:28 to about 1:3. In other embodiment, the P:Ca molar ratio is about 1:25 to about 1:4. In further embodiment the P:Ca molar ratio is about 1:20 to about 1:5. In another embodiment the P:Ca molar ratio is about 1:20 to about 1:6. In a particular embodiment, the P:Ca molar ratio is about 1:15 to about 1:5. In another particular embodiment the P:Ca molar ratio is about 1:25 to about 1:5.

In certain embodiments, the Ca content is about 25 wt % to 38 wt %. In another embodiment the Ca content is about 30 wt % to about 38 wt %. In yet another embodiment the Ca content, is about 30 wt % to about 36 wt %.

In certain embodiments the P:Ca molar ratio is about 1:40 to about 1:1 and the Ca content is 25 wt % to 38 wt %. In some embodiments the molar ratio is 1:28 to about 1:3, and the Ca content is about 30 wt % to about 38 wt %. In another embodiment the molar ratio is 1:25 to about 1:5 and the Ca content is 30 wt % to 36 wt %.

According to any one of the above embodiments the calcium source is any water soluble salt of calcium, and the carbonate source is any water soluble salt of carbonate. In one embodiment the calcium source is calcium chloride. According to another embodiment the carbonate source is sodium carbonate.

According to some embodiments the method comprising filtering the reaction suspension to obtain a wet powdery product ("cake"). Filtering may be performed by any method know in art such as filtering by Buchner funnel, nutsche filter funnel According to some embodiments the method further comprises washing the cake with an aqueous solution. In one particular embodiments the aqueous solution is pure water. In particular the washing is needed to remove by product and excess salts such as sodium chloride or any excess of the sources reactants described above.

According to some embodiments the method comprises drying the cake. The drying may be performed by any method known in art. Non-limiting examples for drying is drying in an oven, vacuum oven, conveyer belt furnace, spray-dryer, freeze drying or a microwave oven. The powder can be also dried by an active flow of dry air or by placing the powder in a room with good air circulation.

According to some embodiments the method comprises further conversion of the cake to small particles. In one embodiments the method comprise milling the cake to obtain a powder. In other embodiments the disintegration comprises grounding, graining and any other commonly used methods.

According to some embodiments the method comprises milling the cake to a powder wherein the size of the powder particles are from about 300 µm to about 5 µm. In one particular embodiments the particles having the size less than 50 µm, less than 40 µm, less than 30 µm, less than 20 µm or less than 10 µm. According to some embodiments at least 70%, at least 80% or at least 90% of the ACC particles have the particle size of less than 5 µm.

The solid composition obtained by the method of the above embodiments is stable as defined hereinabove. According to some embodiments the solid composition is stable for at least 7 days. According to another embodiment, the composition is stable for at least 1 month. According to other embodiments the composition is stable for at least 3 months. According to a further embodiment the composition is stable for 6 months. According to certain embodiment the composition is stable for at least 1 year. According to a particular embodiment, the composition is stable to at least 2 years.

According to some embodiments, the stabilizer is a bisphosphonate or pharmaceutically acceptable salt thereof, and the solid composition comprises 5 wt % to about 30 wt % water.

According to some embodiments, the method comprising further suspending the solid composition of the present invention in an aqueous carrier.

According to any one of the above embodiment no organic solvent is added during the preparation method. Therefore the resulted composition does not comprise any traces of organic solvents. As such the present method is much more environment friendly and safer for manufacturing than the methods known in art, that utilize ethanol or other organic liquids as a solvent or co-solvent.

According to one embodiment the method of preparing a composition of the present invention comprising the steps of:

a) dissolving a calcium source and an inorganic polyphosphate in water;
b) adding an aqueous solution of a carbonate source to the solution of step (a) to precipitate amorphous calcium carbonate;
c) adding an aqueous solution of the inorganic polyphosphate to the suspension obtained in step (b) to obtain the stabilized ACC;
d) filtering the reaction suspension to obtain a cake;
e) washing the cake with water;
f) drying the cake; and
g) milling the cake to a powder,
wherein no organic solvent is added during the preparation, the inorganic polyphosphate is triphosphate, hexametaphosphate or pyrophosphate, the P:Ca molar ratio is about 1:25 to about 1:5. According to some embodiments the Ca content is about 25% to about 38 wt %. In other embodiments the Ca content is about 30 wt % to about 38 wt %. In further embodiments the Ca content is about least 30 wt % to about 36 wt %. In certain embodiments the P:Ca molar ratio is about 1:25 to about 1:5, and the Ca content is about 30 wt % to about 38 wt %. According to some embodiments at least 90% of the ACC particles have the particle size of less than 5 µm.

According to some embodiments the method comprises adding one or more secondary stabilizer. Such secondary stabilizers can be organic compounds known to serve as stabilizers for ACC, e.g., organic compounds containing carboxylic, amine, phosphate, phosphonate and other functional groups that tend to bond, chelate, or complexate to Ca atoms such as citric acid, lactate, phosphoserine, gluconate.

According to another embodiment the method of preparing a composition of the present invention comprising the steps of:

a) dissolving a calcium source and a bisphosphonate in water;
b) adding an aqueous solution of a carbonate source to the solution of step (a) to precipitate amorphous calcium carbonate;
c) adding an aqueous solution of the bisphosphonate to the suspension obtained in step (b) to obtain the stabilized ACC;
d) filtering the reaction suspension to obtain a cake;
e) washing the cake with water;
f) drying the cake; and
g) milling the cake to a powder,
wherein no organic solvent is added during the preparation, the P:Ca molar ratio is about 1:25 to about 1:5, and the composition comprises more than 5 wt % to about 30 wt % water. According to some embodiments the Ca content is about 25% to about 38 wt %. In other embodiments the Ca content is about 30 wt % to about 38 wt %. In further embodiments the Ca content is about least 30 wt % to about 36 wt %. In certain embodiments the P:Ca molar ratio is about 1:25 to about 1:5, and the Ca content is about 30 wt % to about 38 wt %. According to some embodiments at least 90% of the ACC particles have the particle size of less than 5 µm. According to another embodiment the composition comprises more than 10 wt % to about 30 wt % or about 10 wt % to about 20 wt % water.

According to some embodiments the method comprises adding one or more secondary stabilizer. Such secondary stabilizers can be organic compounds known to serve as stabilizers for ACC, e.g., organic compounds containing carboxylic, amine, phosphate, phosphonate and other functional groups that tend to bond, chelate, or complexate to Ca atoms such as citric acid, lactate, phosphoserine, gluconate.

According to another aspect, the present invention provides a method for treating a disease or a condition responsive to a calcium carbonate treatment, comprising administering an effective amount of a composition of the present invention.

According to some embodiments, the composition is a solid composition as defined hereinabove.

According to one embodiment the method comprising administering a solid composition comprising amorphous calcium carbonate (ACC), and an inorganic polyphosphate or a pharmaceutically acceptable salt thereof as a stabilizer, wherein the molar ratio between P atoms of the stabilizer and Ca atoms of the ACC (P:Ca molar ratio) is at least about 1:90 and the composition is stable for at least 7 days.

According to another embodiment, the method comprising administering a solid composition comprising amorphous calcium carbonate (ACC) stabilized by a stabilizer selected from the group consisting of an inorganic polyphosphate, a bisphosphonate, and pharmaceutically acceptable salts thereof, wherein the molar ratio between P atoms of the stabilizer and Ca atoms of the ACC (P:Ca molar ratio) is at least about 1:90, and the composition comprising 5 wt % to about 30 wt % water and is stable for at least 7 days.

According to some embodiments the present invention provides use of a composition according to any one of the above embodiments for preparing a medicament for treating a disease or a condition responsive to a calcium carbonate treatment. According to some embodiments the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious disease and dental disease. According to one particular embodiment, the disease is cancer.

The term "treating" a condition or patient as used herein refers to taking steps to obtain beneficial or desired results, including clinical results. Beneficial or desired clinical results include, but are not limited to, alleviation or amelioration of one or more symptoms associated with the disease.

The term "effective amount" as used herein refers to a sufficient amount of the compositions comprising stabilized ACC to treat the disease or the condition.

The term "responsive" as used herein refers to any disease or conditions that respond to and may be treated by calcium carbonate.

The term "administering" or "administration of" a substance, a compound or an agent to a subject can be carried out using one of a variety of methods known to those skilled in the art. For example, a compound or an agent can be administered enterally or parenterally. Enterally refers to administration via the gastrointestinal tract including per os, sublingually or rectally. Parenteral administration includes administration intravenously, intradermally, intramuscularly, intraperitoneally, subcutaneously, ocularly, sublingually, intranasally, by inhalation, intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug or a medical food. For example, as used herein, a physician who instructs a patient to self-administer a drug or a medical food, or to have the drug or the medical food administered by another and/or who provides a patient with a prescription for a drug or a medical food is administering the drug or a medical food to the patient.

According to some embodiments the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious disease and dental disease. According to one particular embodiment, the disease is cancer.

As used herein, the term "about", when referring to a measurable value, such as an amount, a temporal duration, and the like but excluding peaks of FT-IR spectra for which the term "about" is particularly defined, is meant to encompass variations of +/−10%, or +/−5%, +/−1%, or even +/−0.1% from the specified value.

Having now generally described the invention, the same will be more readily understood through reference to the following examples, which are provided by way of illustration and are not intended to be limiting of the present invention.

EXAMPLES

Materials and Methods

Materials that were used in the experiments are: calcium chloride (78%); sodium carbonate; citric acid; Phosphoserine (PS); Sodium triphosphate (90%); sodium hexametaphosphate (HMP) (90%); ethanol (95%); sodium pyrophosphate (Pyr) (90%); sodium phosphate monobasic (anhydrous), Etidronic acid (ET) (60% aqueous solution); Zoledronic acid (ZA); Medronic acid (MA) and Hydrochloric acid.

Definition of a Stabilizer Concentration

Concentration of a stabilizer in all the examples provided below is defined as follows:

% of a stabilizer=(amount of initially added stabilizer(in g)/amount of initially added CaCl2(in g))×100

The correlation between different concentrations of stabilizers and the P:Ca molar ratio is summarized in Table 4

Stability Assessment

The stability of the ACC in the suspension or as a powder was tested by sampling at different time intervals and evaluating the amount of crystalline calcium carbonate as a percent of the initial amount. The amount of crystalline phase of Calcium carbonate in the sample was estimated using X-Ray diffraction (XRD) method.

XRD Collection—Experimental Section

The X-ray data are collected on Panalytical powder diffractometer (Philips 1050/70 or Empyrean), equipped with graphite monochromator on diffracted beam providing Cu-K$_\square$ radiation and operating at V=40 kV, I=30 mA. Scans are run in a 2$\square$ range of 15-50 or 24-36° with a step equal to ~0.03°. This interval contains a main peaks of Calcite (reflection (104) at 2 theta deg=29.3°±0.2°) and Vaterite (reflections (100), (101) and (102) at 2 theta deg equal to 24.8°, 27.0° and 32.7°±0.2° respectively).

The X-ray data are collected on Rigaku powder diffractometer (MiniFlex 600 Benchtop), equipped with graphite monochromator on diffracted beam providing Cu-Kα radiation and operating at V=40 kV, I=15 mA. Scans are run in a 2θ range of 26-34° with a step equal to ~0.02°. This interval contains a main peaks of Calcite (reflection (104) at 2 theta deg=29.3°±0.2°) and Vaterite (reflections (101) and (102) at 2 theta deg equal to 24.8°, 27.0° and 32.7°±0.2° respectively).

The samples were compared to a calibration plot built using standard samples comprising known amounts and ratios of amorphous and crystalline (such as Calcite or Vaterite) Calcium Carbonate.

Figure 2:
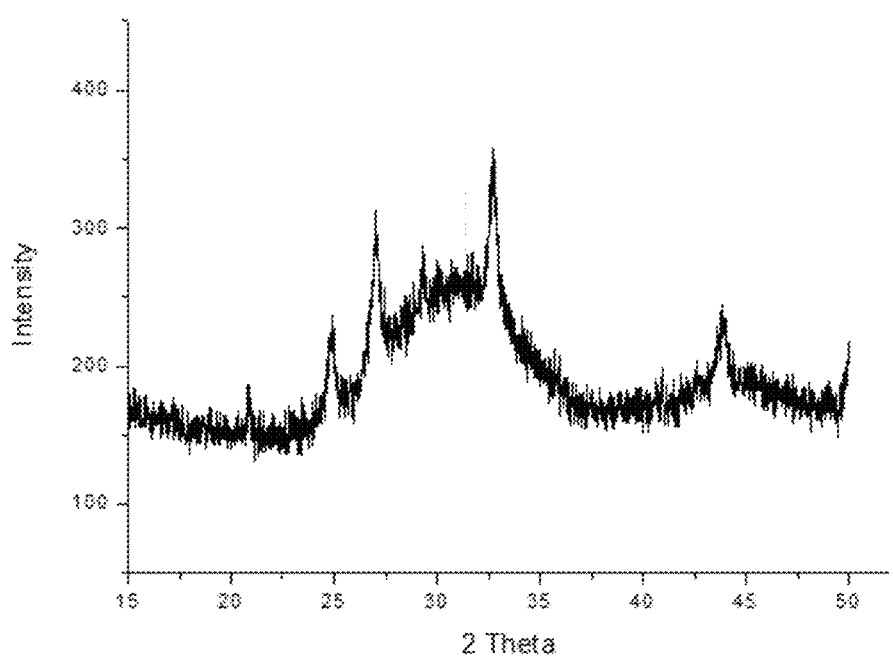
FIG. 2 shows a representative XRD diffractogram of ACC stabilized with pyrophosphate (Pyr-5%) of which a small portion converted to crystalline form (94% ACC).
Figure 3:
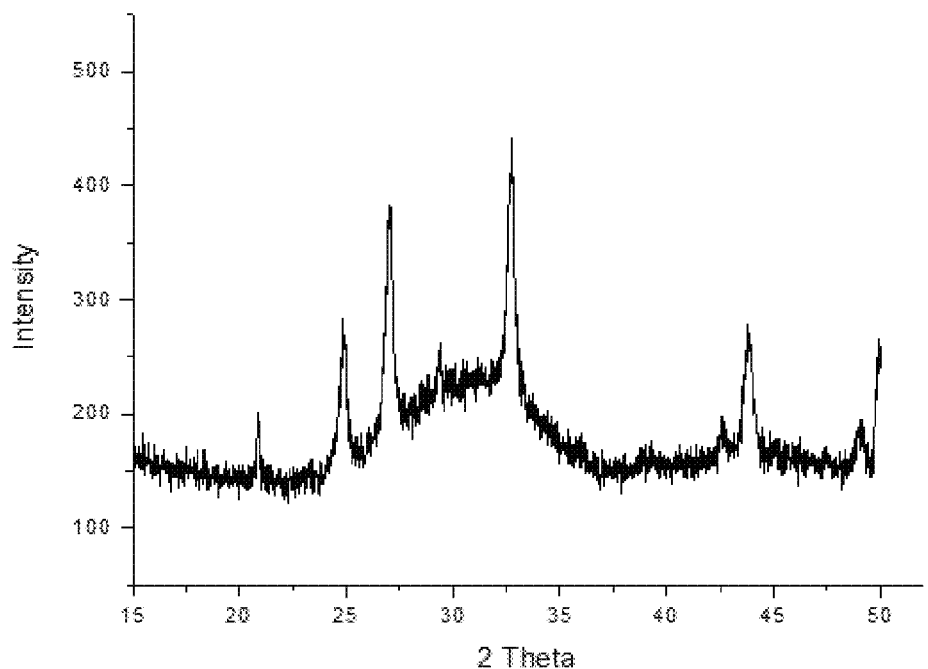
FIG. 3 shows a representative XRD diffractogram of ACC stabilized with hexametaphosphate (HMP-5%, 89% ACC).

Example 1. Stability of Powder Compositions of ACC Stabilized with Polyphosphates, or Phosphate Monobasic Powder compositions of ACC stabilized by different stabilizers (triphosphate (TP), hexametaphosphate (HMP), pyrophosphate (Pyr), phosphate monobasic (PM) or citric acid (CA)) were prepared. In a typical procedure, a calcium solutions (300 ml of water, 24 g of calcium chloride and a stabilizer) and a carbonate solution (200 ml of water and 17.3 g of sodium carbonate) were mixed together to precipitate ACC. A stabilizer solution (100 ml of water and stabilizer; the content of the stabilizers in the calcium and stabilizer solution is presented in Table 1; the correlation between different concentrations of stabilizers and the P:Ca molar ratio is summarized in Table 4) was added to the ACC suspension creating stabilized ACC suspension. The ACC was then filtered using a Buchner funnel, the cake was washed with water. Powder obtained by drying the cake. The stability of ACC in the powder was tested as by XRR as described in material and methods part; the results are presented in Tables 2 and 3. Representative XRD spectra are presented in FIGS. 1-3.

TABLE 1

The content of the stabilizers in different ACC composition

| | Composition | | | | | | |
|---|---|---|---|---|---|---|---|
| | 1% TP | 2% TP | 3% TP | 4% TP | 6% TP/HMP/Pyr/PM | 10% TP/HMP/Pyr/PM | 15% PM |
| Stabilizer in Calcium solution (g) | 0.12 | 0.24 | 0.36 | 0.48 | .072 | 1.2 | 1.8 |
| Stabilizer in Stabilizing solution (g) | 0.12 | 0.24 | 0.36 | 0.48 | .072 | 1.2 | 1.8 |

TABLE 2

Stability of powder preparation of ACC stabilized with TP

| | COMPOSITIONS | | | | | | | | | | | |
|---|---|---|---|---|---|---|---|---|---|---|---|---|
| | 1% TP | | 2% TP | | 3% TP | | 4% TP | | 6% TP | | 10% TP | |
| Day | % ACC | % CCC | % ACC | % CCC | % ACC | % CCC | % ACC | % CCC | % ACC | % CCC | % ACC | % CCC |
| 0 | 7 | 93 | | | | | 100 | 0 | 100 | 0 | 100 | 0 |
| 1 | | | | | | | 100 | 0 | | | | |
| 3 | | | | | | | 100 | 0 | | | | |
| 6 | | | | | | | 100 | 0 | | | | |
| 8 | | | | | | | | | 100 | 0 | 100 | 0 |
| 11 | | | | | 100 | 0 | | | | | | |
| 31 | | | | | | | 100 | 0 | | | | |
| 35 | | | 94 | 6 | | | | | | | | |
| 38 | | | | | | | | | 100 | 0 | 100 | 0 |
| 50 | | | | | | | 100 | 0 | | | | |
| 93 | | | | | | | | | 100 | 0 | 100 | 0 |
| 98 | | | | | | | 95 | 5 | | | | |

TABLE 3

Stability of powder preparation of ACC stabilized with HMP, Pyr or PM

| | COMPOSITIONS | | | | | | | | | | | | | |
|---|---|---|---|---|---|---|---|---|---|---|---|---|---|---|
| | 6% HMP | | 10% HMP | | 6% Pyr | | 10% Pyr | | 6% PM | | 10% PM | | 15% PM | |
| Day | % ACC | % CCC | % ACC | % CCC | % ACC | % CCC | % ACC | % CCC | % ACC | % CCC | % ACC | % CCC | % ACC | % CCC |
| 0 | 96.5 | 3.5 | 98 | 2 | 97 | 3 | 97 | 3 | 76 | 24 | 79 | 21 | 93 | 7 |
| 1 | | | | | | | | | 58 | 42 | | | | |
| 2 | | | | | | | | | 53 | 47 | | | | |
| 6 | | | | | | | | | | | | | 92 | 8 |
| 8 | | | | | | | | | 60 | 40 | | | | |
| 9 | | | | | | | 97 | 3 | | | 81 | 19 | | |
| 14 | 99 | 1 | 99.3 | 0.7 | | | | | | | 78 | 22 | | |
| 15 | | | | | 91.5 | 8.5 | | | | | | | | |
| 29 | | | | | | | 97 | 3 | | | | | | |
| 30 | | | 100 | 0 | | | | | | | | | | |
| 92 | | | | | | | 96 | 4 | | | | | | |

TABLE 3-continued

Stability of powder preparation of ACC stabilized with HMP, Pyr or PM

| | COMPOSITIONS | | | | | | | | | | | | | |
|---|---|---|---|---|---|---|---|---|---|---|---|---|---|---|
| | 6% HMP | | 10% HMP | | 6% Pyr | | 10% Pyr | | 6% PM | | 10% PM | | 15% PM | |
| Day | % ACC | % CCC | % ACC | % CCC | % ACC | % CCC | % ACC | % CCC | % ACC | % CCC | % ACC | % CCC | % ACC | % CCC |
| 96 | 96 | 4 | 97 | 3 | | | | | | | | | 88 | 12 |
| 97 | | | | | 86 | 14 | | | | | | | | |

TABLE 4

Correlation between the stabilizer's concentration (in %) and P:Ca molar ratio

| Conc (%) | TP | HMP | Pyr | PM | PS | ET | ZA | MA |
|---|---|---|---|---|---|---|---|---|
| 1 | 1:95 | | | | | | | |
| 2 | 1:48 | 1:39 | 1:40 | | | 1:36 | 1:48 | 1:30 |
| 3 | 1:31 | | | | | | | |
| 4 | 1:24 | 1:20 | 1:26 | | | | | |
| 5 | 1:21 | 1:16 | 1:20 | | 1:26 | 1:14.5 | 1:19 | 1:12 |
| 6 | 1:16 | 1:13 | 1:17 | 1:16 | 1:19* | | | |
| 7 | | | | | | 1:10 | 1:14 | 1:9 |
| 10 | 1:10 | 1:8 | 1:10 | 1:9 | | 1:7 | 1:10 | 1:6 |
| 15 | 1:6 | 1:5.3 | 1:7 | 1:6 | | | | |

*the PS concentration is 6.8%

Example 2. Stability of the ACC, Stabilized with Polyphosphates or Phosphoserine, in a Suspension Several suspensions of ACC stabilized with different stabilizers were prepared. In a typical procedure, the calcium solutions (1 L of water, 21.6 g of calcium chloride and a stabilizer (TP, HMP, Pyr or PS) and carbonate solution (800 ml of water and 15.6 g of sodium carbonate) were mixed together to precipitate ACC. The stabilizer solution (200 ml of water and stabilizer; the content of the stabilizers in calcium and stabilizer solution is presented in Table 4) was added to the ACC suspension creating stabilized ACC suspension. The results of the stability test are presented in Table 5.

TABLE 5

Stabilizer content in different compositions

| Composition name | 1% PS | 2% TP/ HMP/ Pyr | 4% TP/ HMP/ Pyr | 5% TP/ HMP/ Pyr/PS | 6% TP/ HMP/ Pyr | 10% TP HMP/ Pyr | 15% TP/ HMP/ Pyr |
|---|---|---|---|---|---|---|---|
| Stabilizer in Calcium solution (g) | 0.11 | 0.22 | 0.43 | 0.54 | 0.65 | 1.08 | 1.62 |
| Stabilizer Stabilizing solution (g) | 0.11 | 0.22 | 0.43 | 0.54 | 0.65 | 1.08 | 1.62 |

TABLE 6

Stability of ACC stabilized with TP in a suspension

| | COMPOSITIONS | | | | | | | | | |
|---|---|---|---|---|---|---|---|---|---|---|
| | 2% TP | | 4% TP | | 6% TP | | 10% TP | | 15% TP | |
| Day | % ACC | % CCC | % ACC | % CCC | % ACC | % CCC | % ACC | % CCC | % ACC | % CCC |
| 0 | | | | | 98 | 2 | 100 | 0 | 100 | 0 |
| 1 | | | 92 | 8 | | | | | | |
| 3 | 37 | 63 | | | | | | | | |
| 7 | | | | | | | | | 96.5 | 3.5 |
| 12 | | | 78 | 22 | | | | | | |
| 29 | | | | | 73 | 27 | 89 | 11 | 88 | 12 |
| 61 | | | | | | | | | | |
| 62 | | | | | 60 | 40 | 68 | 32 | 85 | 15 |
| 91 | | | | | 75 | 25 | 70 | 30 | 80 | 20 |

TABLE 7

Stability of ACC stabilized with HMP in a suspension

| | COMPOSITIONS | | | | | | | | | | | |
|---|---|---|---|---|---|---|---|---|---|---|---|---|
| | 2% HMP | | 4% HMP | | 5% HMP | | 6% HMP | | 10% HMP | | 15% HMP | |
| Day | % ACC | % CCC | % ACC | % CCC | % ACC | % CCC | % ACC | % CCC | % ACC | % CCC | % ACC | % CCC |
| 1 | | | | | | | 100 | 0 | | | | |
| 3 | 37 | 63 | 87 | 13 | | | | | | | | |

TABLE 7-continued

Stability of ACC stabilized with HMP in a suspension

| | COMPOSITIONS | | | | | | | | | | | |
|---|---|---|---|---|---|---|---|---|---|---|---|---|
| | 2% HMP | | 4% HMP | | 5% HMP | | 6% HMP | | 10% HMP | | 15% HMP | |
| Day | % ACC | % CCC | % ACC | % CCC | % ACC | % CCC | % ACC | % CCC | % ACC | % CCC | % ACC | % CCC |
| 8 | | | | | 88 | 12 | | | 94 | 6 | 99 | 1 |
| 12 | | | | | | | 81 | 19 | 95 | 6 | 98.5 | 1.5 |
| 29 | | | | | | | | | 97 | 3 | 97 | 3 |
| 61 | | | | | | | | | | | | |
| 62 | | | | | | | 97 | 3 | 94 | 6 | 97 | 3 |
| 91 | | | | | | | 96 | 4 | 99.5 | 0.5 | | |

TABLE 8

Stability of ACC stabilized with Pyr in a suspension

| | COMPOSITIONS | | | | | | | | | | | |
|---|---|---|---|---|---|---|---|---|---|---|---|---|
| | 2% Pyr | | 4% Pyr | | 5% Pyr | | 6% Pyr | | 10% Pyr | | 15% Pyr | |
| Day | % ACC | % CCC | % ACC | % CCC | % ACC | % CCC | % ACC | % CCC | % ACC | % CCC | % ACC | % CCC |
| 0 | 60 | 40 | | | | | | | | | 98 | 2 |
| 3 | 49 | 51 | 87 | 13 | 94 | 6 | | | | | | |
| 7 | | | 85 | 15 | 94 | 6 | 100 | 0 | 100 | 0 | 100 | 0 |
| 12 | | | | | | | | | | | | |
| 29 | | | | | | | 89 | 11 | 92 | 8 | 92 | 00 |
| 61 | | | | | | | 96 | 4 | 96 | 4 | 94.5 | 5.5 |
| 91 | | | | | | | 95 | 5 | 93 | 7 | 95 | 5 |

Figure 4:
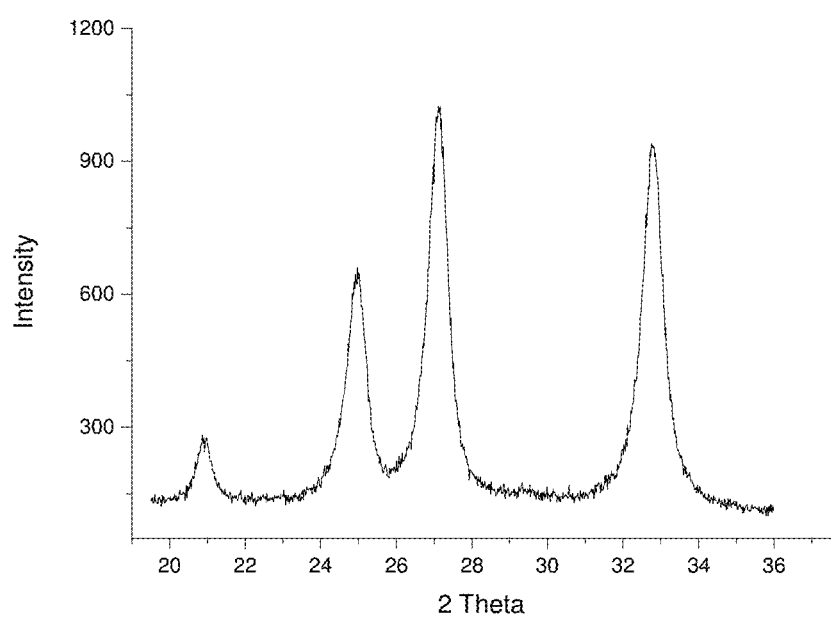
FIG. 4 shows a representative XRD diffractogram of ACC with PS 5% and 5% CA (100% CCC).

It was found that phosphoserine in concentration of 1% or 5% could not stabilize ACC in a suspension; all calcium carbonate was crystalline already after 4 hours (for a PS-5% composition see e.g. FIG. 4).

Example 3. Stability of the Re-Suspended ACC Stabilized with Etidronic Acid

Several suspensions of ACC stabilized by etidronic acid were prepared. In a typical procedure, the calcium solutions (600 mL of water, 12 g of calcium chloride and etidronic acid (60% aqueous solution)) and carbonate solution (100 ml of water and 8.65 g of sodium carbonate) were mixed together to precipitate ACC. The stabilizer solution (300 ml of water and etidronic acid; the content of the etidronic acid in calcium as stabilizer solution is presented in Table 9) was added to the ACC suspension creating stabilized ACC suspension. The ACC was then filtered using a Buchner funnel, the cake was washed with water. Suspension was obtained by dispersing the cake with 1100 ml water. The stability of the ACC in a suspension was tested, and results are presented in Table 10.

TABLE 9

Stabilizer content in different composition

| Composition name | 5% ET | 7% ET | 10% ET |
|---|---|---|---|
| ET (60% aqueous solution) in Calcium solution (g) | .05 | 0.7 | 1 |
| ET (60% aqueous solution) in Stabilizing solution (g) | .05 | 0.7 | 1 |

TABLE 10

Stability of ACC stabilized with etidronic acid in a suspension preparation

| | COMPOSITIONS | | | | | |
|---|---|---|---|---|---|---|
| | 5% ET | | 7% ET | | 10% ET | |
| Day | % ACC | % CCC | % ACC | % CCC | % ACC | % CCC |
| 2 | 100 | 0 | 100 | 0 | 100 | 0 |
| 7 | 100 | 0 | 100 | 0 | 100 | 0 |
| 14 | 100 | 0 | 100 | 0 | 100 | 0 |
| 30 | 100 | 0 | 100 | 0 | 100 | 0 |
| 90 | 100 | 0 | 100 | 0 | 100 | 0 |
| 195 | 100 | 0 | 98 | 2 | 98 | 2 |

Example 4. Stability of the Re-Suspended ACC Stabilized by a Combination of Citric Acid with HMP, TP or PS Two powder compositions (referred as 6% HMP-1% CA and 10% HMP-1% CA) of ACC stabilized by citric acid and HMP were prepared as following: the calcium solutions (100 mL of water, 11.76 g of calcium chloride, 0.12 g citric acid, and 0.35 g or 0.59 g of HMP) and carbonate solution (100 ml of water and 8.48 g of sodium carbonate) were mixed together to precipitate ACC. The stabilizer solution (20 ml of water and 0.35 g or 0.59 g HMP) was added to the ACC suspensions creating stabilized ACC suspension (the suspension of 6% HMP-1% CA and of 10% HMP-1% CA comprised 0.7 and 1.18 g HMP, respectively). The ACC was then filtered using a Buchner funnel, the cake was washed with water.

Two powder compositions (referred as 6.8% PS-6% CA-Et-OH and 5% PS-6% CA-Et-OH) of ACC stabilized by citric acid and phosphoserine were prepared as following: the calcium solutions (100 ml of water, 11.76 of calcium chloride, 0.12 g citric acid and 0.8 g or 0.59 g of phosphoserine (for 6.8% PS-6% CA, and 6% PS-6% CA composition, respectively)) and carbonate solution (100 ml of water and 8.48 g of sodium carbonate) were mixed together to precipitate ACC. The stabilizer solution (20 ml of water and 0.59 citric acid) and 50 ml ethanol were added to the ACC suspension creating stabilized ACC suspension. The ACC was then filtered using a Buchner funnel, the cake was washed with ethanol.

The resulted powder was dispersed in 1100 ml of water to obtain a suspension and the stability of the ACC was tested as described in material and methods. The results are presented in Table 11.

A powder compositions (10% TP-1% CA) of ACC stabilized by citric acid and phosphoserine were prepared as following: the calcium solutions (300 ml of water, 24 g of calcium chloride, 0.24 g citric acid and 1.2 g of triphosphate) and carbonate solution (200 ml of water and 17.3 g of sodium carbonate) were mixed together to precipitate ACC. The stabilizer solution (100 ml of water and 1.2 g triphosphate) was added to the ACC suspension creating stabilized ACC suspension. The ACC was then filtered using a Buchner funnel, the cake was washed with water. The resulted powder was dispersed in 792 ml of water to obtain a suspension and the stability of the ACC was tested as described in material and methods. The results are presented in Table 11.

A powder compositions (5% PS-5% CA-Et-OH) of ACC stabilized by citric acid and phosphoserine were prepared as following: the calcium solutions (100 mL of water, 11.76 of calcium chloride, 0.12 g citric acid and 0.6 g of phosphoserine and carbonate solution (100 ml of water and 8.48 g of sodium carbonate) were mixed together to precipitate ACC. The stabilizer solution (20 ml of water and 0.48 citric acid) and 50 ml ethanol were added to the ACC suspension creating stabilized ACC suspension. The ACC was then filtered using a Buchner funnel, the cake was washed with ethanol. Powder obtained by drying the cake. 8 g of ACC powder was re-suspended in 792 g water. The results are presented in Table 11.

TABLE 11

Stability of ACC stabilized with different stabilizers in a suspension.

| | COMPOSITIONS | | | | | | | | | | | |
|---|---|---|---|---|---|---|---|---|---|---|---|---|
| | 6% HMP-1% CA | | 10% HMP-1% CA | | 10% TP-1% CA | | 5% PS-5% CA-Et-OH | | 5% PS-6% CA-Et-OH | | 6.8% PS-Et-OH5% CA | |
| Day | % ACC | % CCC | % ACC | % ACC | % ACC | % ACC | % ACC | % ACC | % ACC | % CCC | % ACC | % CCC |
| 0 | | | | | 99.5 | 0.5 | 100 | 0 | | | | |
| 1 | 96 | 4 | 100 | 0 | 99.5 | 0.5 | 2 | 98 | 100 | 0 | 100 | 0 |
| 3 | 95 | 5 | | | | | | | | | | |
| 4 | | | 99 | 1 | | | | | | | | |
| 6 | 91 | 9 | | | 78 | 22 | | | | | 20 | 80 |
| 9 | 83 | 17 | 97 | 3 | | | | | 10 | 90 | | |
| 13 | | | | | | | | | | | 10 | 90 |
| 16 | | | 96 | 4 | | | | | | | | |
| 35 | | | 95 | 5 | | | | | | | | |

Example 5. Stability of the Re-Suspended ACC Stabilized with HMP in Presence of Hydrochloric Acid Four powder compositions of ACC stabilized by HMP were prepared as following: the calcium solutions (100 ml of water, 12 g of calcium chloride, 1 g of hydrochloric acid 8% and HMP) and carbonate solution (100 ml of water and 8.65 g of sodium carbonate) were mixed together to precipitate ACC. The stabilizer solution (50 ml of water and HMP; the content of the HMP acid in calcium and stabilizer solution is presented in Table 12) was added to the ACC suspensions creating stabilized ACC suspension. The ACC was then filtered using a Buchner funnel, the cake was washed with water. The resulted powder was dispersed in 1100 ml of water to obtain a suspension. The stability of the ACC in the suspension was tested as described above and the results are presented in Table 13.

TABLE 12

Amount of HMP (in grams) in different powder composition

| Composition name | 2% HMP-HCl | 5% HMP-HCl | 7% HMP-HCl | 10% HMP-HCl |
|---|---|---|---|---|
| HMP in Calcium solution (g) | 0.12 | 0.3 | 0.42 | 0.6 |
| HMP in Stabilizing solution (g) | 0.12 | 0.3 | 0.42 | 0.6 |

TABLE 13

Stability of powder preparation of ACC stabilized with different stabilizers

| | COMPOSITIONS | | | | | | | |
|---|---|---|---|---|---|---|---|---|
| | 2% HMP-HCl | | 5% HMP-HCl | | 7% HMP-HCl | | 10% HMP-HCl | |
| Day | % ACC | % CCC | % ACC | % CCC | % ACC | % CCC | % ACC | % CCC |
| 0 | 3 | 97 | 92 | 8 | 98 | 2 | 100 | 0 |
| 3 | 3 | 97 | 78 | 22 | | | 98 | 2 |
| 9 | | | 59 | 41 | 73 | 27 | 90 | 10 |
| 14 | | | | | 70 | 30 | 87 | 13 |
| 29 | | | | | | | 75 | 25 |

Example 6. Effect of Different Polyphosphate on Stability of the Re-Suspended ACC Three powder compositions (referred as 10% HMP, 10% Pyr, and 10% TP) of ACC were prepared as follows: the calcium solutions (100 ml of water, 12 g of calcium chloride and 0.6 g of HMP, PyroP or TP) and carbonate solution (100 ml of water and 8.65 g of sodium carbonate) were mixed together to precipitate ACC. The stabilizer solution (300 ml of water and 0.6 g of HMP, PyroP or TP) was added to the ACC suspensions creating stabilized ACC suspension (10% HMP, 10% Pyr, and 10% TP suspensions comprised 1.2 g of HMP, PyroP or TP, respectively). The ACC was then filtered using a Buchner funnel, the cake was washed with water. The resulted powder was dispersed in 1100 ml water to obtain a suspension and the stability was tested. The results are presented in Table 14.

TABLE 14

Stability of powder preparation of ACC stabilized with different stabilizers

| | COMPOSITIONS | | | | | |
|---|---|---|---|---|---|---|
| | 10% HMP | | 10% Pyr | | 10% TP | |
| Day | % ACC | % CCC | % ACC | % CCC | % ACC | % CCC |
| 2 | 100 | 0 | 97 | 3 | 100 | 0 |
| 7 | 86 | 14 | 92 | 8 | 86 | 14 |
| 14 | 80 | 20 | 84 | 16 | 80 | 20 |

Example 7. Stability of the ACC Stabilized with Bisphosphonates

Several suspensions of stabilized ACC with different content of stabilizers were prepared. In a typical procedure, the calcium solutions (100 mL or 200 mL of water, 12 g of calcium chloride and stabilizer) and carbonate solution (100 ml of water and 8.65 g of sodium carbonate) were mixed together to precipitate ACC. The stabilizer solution (300 ml of water and stabilizer; the content of the stabilizers in calcium and stabilizer solution is presented in Table 15) was added to the ACC suspension creating stabilized ACC suspension. The ACC was then filtered using a Buchner funnel, the cake was washed with water. Suspension obtained by dispersing the cake with water. The resulted powder was dispersed in 1100 ml of water the stability of ACC in a suspension was tested. The results are presented in Table 16.

TABLE 15

Stabilizer content in different composition

| | Composition name | | | | | | | |
|---|---|---|---|---|---|---|---|---|
| | 2% ET | 5% ET | 7% ET | 10% ET | 5% ZA | 10% ZA | 5% MA | 10% MA |
| Calcium solution (g) | 0.12 | 0.3 | 0.42 | 0.6 | 0.3 | 0.6 | 0.3 | 0.6 |
| Stabilizing solution (g) | 0.12 | 0.3 | 0.42 | 0.6 | 0.3 | 0.6 | 0.3 | 0.6 |

TABLE 16

Stability of powder preparation of ACC stabilized with different stabilizers

| | COMPOSITIONS | | | | | | | | | | | | | | | |
|---|---|---|---|---|---|---|---|---|---|---|---|---|---|---|---|---|
| | 2% ET | | 5% ET | | 7% ET | | 10% ET | | 5% ZA | | 10% ZA | | 5% MA | | 10% MA | |
| Day | % ACC | % CCC | % ACC | % CCC | % ACC | % CCC | % ACC | % CCC | % ACC | % CCC | % ACC | % CCC | % ACC | % CCC | % ACC | % CCC |
| 2 | | | 100 | 0 | 100 | 0 | 100 | 0 | | | 100 | 0 | | | | |
| 6 | | | | | | | | | 100 | 0 | | | 95 | 5 | 100 | 0 |
| 7 | 49 | 51 | 100 | 0 | 100 | 0 | 100 | 0 | | | 100 | 0 | | | | |
| 14 | | | 100 | 0 | 100 | 0 | 100 | 0 | | | 100 | 0 | | | | |

Example 8. Stability of the Re-Suspended ACC Stabilized with Citric Etidronic Acids and Ethanol In a typical procedure, the calcium solution contained 100 ml of water, 11.76 g of calcium chloride, 0.12 g of citric acid and 0.59 g of etidronic acid. The carbonate solution contained 100 ml of water and 8.48 g of sodium carbonate. The stabilizing solution contained 20 ml of water and 0.59 g of citric acid. 50 ml of ethanol was used as the organic solvent. The calcium and carbonate solutions were mixed together to precipitate ACC, the stabilizer solution and the ethanol was added to the ACC suspension creating stabilized ACC suspension. The ACC was then filtered using a Buchner funnel, the cake was washed with ethanol. Suspension obtained by dispersing the cake with water. The stability of the ACC was tested and the results are presented in Table 17.

TABLE 17

Stability of ACC stabilized by ET, CA and Et-OH in a suspension

| Time (days) | % ACC | % CCC |
|---|---|---|
| 1 | 100 | 0 |
| 6 | 100 | 0 |
| 9 | 100 | 0 |
| 15 | 99 | 1 |
| 23 | 100 | 0 |
| 30 | 99 | 1 |
| 36 | 100 | 0 |

Example 9. Stability of the ACC-Triphosphate Suspensions Having Different ACC Concentration 10% TP-0.06% Ca Calcium solution containing 2 L of water, 8.66 g of calcium chloride and 0.433 g of was mixed with the carbonate solution containing 1800 ml of water and 6.24 g of sodium carbonate, to precipitate ACC. The stabilizing solution containing 200 ml of water and 0.433 g of triphosphate was added to the ACC suspension creating stabilized ACC suspension.

10% TP-1% Ca

Calcium solution containing 300 ml of water, 24 g of calcium chloride and 1.2 g of triphosphate was mixed with the carbonate solution containing 200 ml of water and 17.3 g of sodium carbonate, to precipitate ACC. The stabilizing solution containing 100 ml of water and 1.2 g of triphosphate was added to the ACC suspension creating stabilized ACC suspension. The stability of these suspensions was tested and the results are presented in Table 18

TABLE 18

Stability of ACC suspensions with different dilutions of ACC

| | COMPOSITIONS | | | | | |
|---|---|---|---|---|---|---|
| | 10% TP-0.06% Ca | | 10% TP-1% Ca | | 10% TP 0.3% Ca | |
| Day | % ACC | % CCC | % ACC | % CCC | % ACC | % CCC |
| 11 | 100 | 0 | 85 | 15 | 100 | 0 |
| 42 | 88 | 12 | 79 | 21 | 100 | 0 |
| 104 | 82 | 18 | | | 100 | 0 |

It can be seen from the result that the concentration of ACC in a suspension does not affect significantly the stability of the ACC.

Example 10. The Content of a Dried ACC Powder

The content of the different compounds such as phosphate atoms and the calcium in the powder preparation of ACC stabilized by different stabilizers and prepared as described in Example 1 was tested using inductivity coupled plasma (ICP) method. The results are summarized Table 19.

TABLE 19

The P:Ca molar ratio, Calcium content and P atoms content in dried ACC compositions determined using ICP.

| Sample | P:Ca molar ratio | Ca wt % | P wt % |
|---|---|---|---|
| ACC-TP1% | 1:95.13 | 37.640 | 0.306 |
| ACC-TP2% | 1:36.95 | 32.625 | 0.682 |
| ACC-TP3% | 1:24.53 | 32.823 | 1.034 |
| ACC-TP4% | 1:19.69 | 34.533 | 1.355 |
| ACC-TP6% | 1:13.09 | 32.686 | 1.930 |
| ACC-TP10% | 1:8.32 | 30.974 | 2.878 |
| ACC-HMP6% | 12.01 | 33.183 | 2.136 |
| ACC-HMP10% | 1:8.25 | 31.995 | 2.998 |
| ACC-PyroP6% | 1:11.63 | 33.225 | 2.209 |
| ACC-PyroP10% | 1:6.62 | 32.907 | 3.842 |

It can be seen that the Ca content of solid powder composition of ACC stabilized with different stabilizers is about 30-40 wt %.

Example 11. Scale-Up Production of ACC-TP10% Powder

In a typical procedure, the calcium solution contained 11 L of water, 1.2 kg of calcium chloride and 60 g of triphosphate. The carbonate solution contained 10 L of water and 864 g of sodium carbonate. The stabilizing solution contained 1 L of water and 60 g of triphosphate. The calcium and carbonate solutions were mixed together to precipitate ACC, the stabilizer solution and was added to the ACC suspension creating stabilized ACC suspension. The ACC was then filtered using a nutsche filter funnel, the cake was washed with water. Powder obtained by drying the cake. The stability of the resulted powder is presented Table 20.

TABLE 20

Stability of ACC-TP10% powder

| Sample | Day | % ACC | % CCC |
|---|---|---|---|
| ACC-TP10% | 3 | 95 | 5 |
| ACC-TP10% | 274 | 90 | 10 |

Example 12. Solid State NMR Analysis

Method

All MAS NMR experiments were carried out on a Bruker Advance III 500 MHZ narrow-bore spectrometer, using a 4 mm double-resonance MAS probe.

$^{13}C$ CPMAS experiments were carried out at a spinning rate of 8 kHz, using a 2.5 μs $^1H$ 90° pulse, 2 ms mixing time and a 5 s recycle delay between acquisitions. Chemical shift was given with respect to adamantane (38.55, 29.497 ppm).

$^{31}$P CPMAS experiments were carried out at a spinning rate of 10 kHz, using a 2.5 μs $^1$H 90° pulse, 3 ms mixing time and a 5 s recycle delay between acquisitions. Chemical shift was given with respect to Na$_2$HPO$_4$ (6.5 ppm).

The deviation of the peak is ±0.5 ppm.

Results and Discussion

All samples were run on X-ray powder diffraction prior NMR CP-MAS measurements and found to have about 100% Amorphous content except for ACC-TP1%, see Table 21 below.

All $^{13}$C SS-NMR exhibited one peak (see Table 21 below) which relates to the carbon of ACC carbonate ion at 168.7±0.5 ppm. Hence, different amounts (%) of certain polyphosphate molecule or different polyphosphates stabilizers in ACC does not affect the chemical shift as observed by $^{13}$C CP-MAS; The carbon atom of the carbonate ion "feels" the same spatial environment in all systems independent of its phosphorous composition or chemical structure.

In the $^{31}$P NMR the number of the peaks (one for PS, two for Pyro-P, three for TP) reflects the number of phosphate atoms in each molecule, showing different spatial environment. The HMP has three peaks although it has six phosphate atoms which might relate to overlay each two peaks or that each two phosphate atoms show approximately the same spatial environment. The ACC-TP different concentrations (3% vs. 6% and 10%) show a difference in the upper field signal (+3.7 vs. +2.8 and +3.0). Since the samples were measured once and were of single preparation we decided to not evaluate these differences.

TABLE 21

$^{13}$C and $^{31}$P CP-MAS and XRPD data of ACC with different stabilizers

| Sample Name of Stabilized ACC's | $^{13}$C CP-MAS NMR (δ Shift in ppm) | $^{31}$P CP-MAS NMR (δ Shift in ppm) | ACC Amorphous content |
|---|---|---|---|
| ACC-TP3% | Singlet 168.7 | Triplet: +3.7, −6.4 (Main), ~(−19.0) | 100% |
| ACC-TP6% | Singlet 168.9 | Triplet: +2.8, −6.5 (Main), −18.4 | 100% |
| ACC-TP10% | Singlet 168.8 | Triplet: +3.0, −6.7 (Main), −18.7 | 100% |
| ACC-Pyro-P10% | Singlet 168.9 | Doublet: +2.2, −6.4 (Main) | 100% |
| ACC-HMP10% | Singlet 168.8 | Triplet: +2.9, −7.3 (Main), −22.4 | 100% |
| ACC-PS1%-CA5% | Singlet 168.8 | Singlet: +1.3 | 99% |
| (Ca)3(PO4)2 | N/A | Singlet: +3.1 | Amorphous phase |

It can be seen from these results that all inorganic polyphosphates are intact and do not break down or decompose to smaller compound.

Example 13. Differential Scanning Calorimetry (DSC) Analysis of ACC Stabilized with Polyphosphates The DSC analysis was performed under non-oxidizing conditions obtained by streaming nitrogen gas 80 ml/min and the temperature was raised from 30° C. to 600° C. at 10° C./min.

Figure 5:
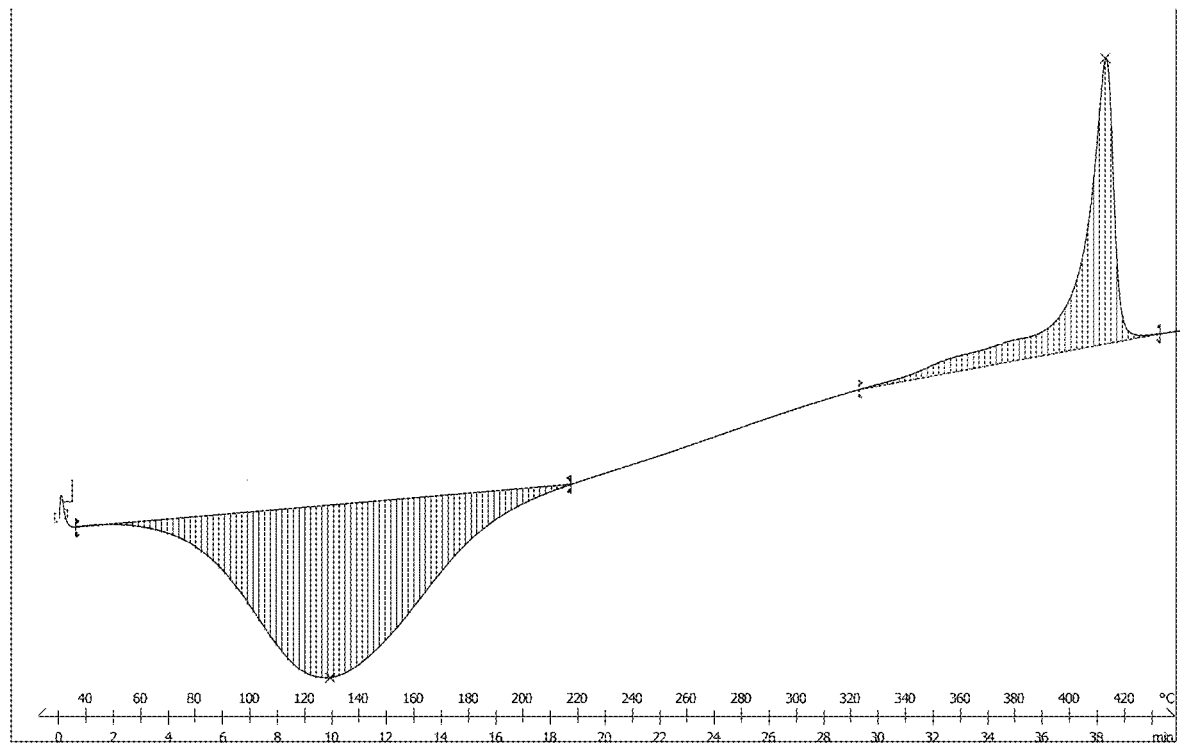
FIG. 5 shows a representative DSC thermogram of ACC stabilized with polyphosphate: TP-6% showing an exothermic peak at 414° C.
Figure 6A:
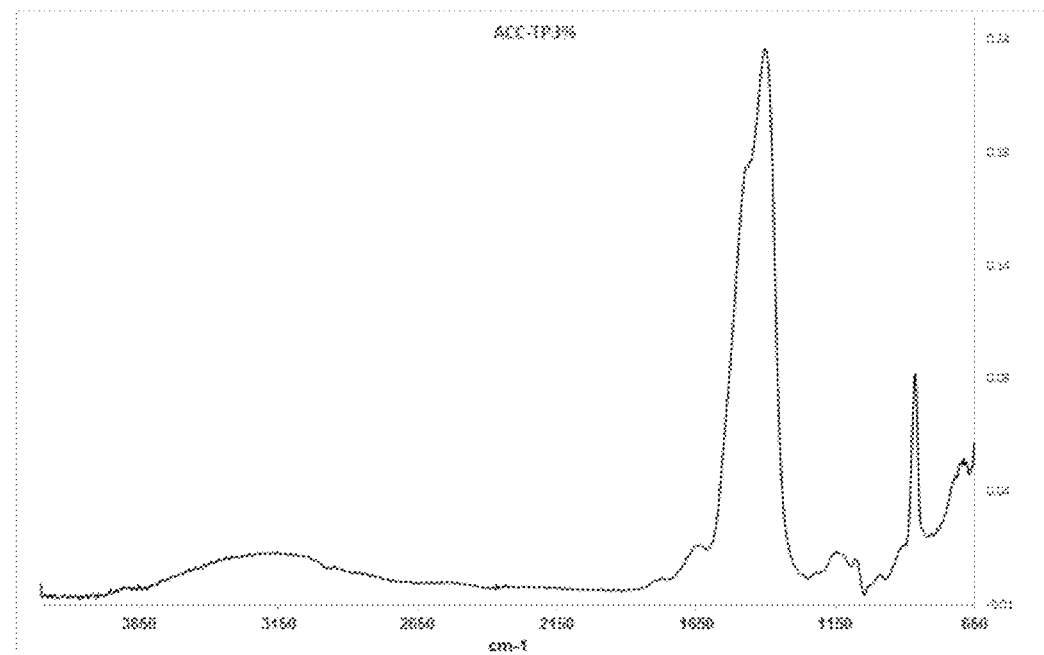
FIGS. 6A-6H shows a representative FT-IR absorption spectra of: ACC-TP3% (FIG. 6A); ACC-TP4% (FIG. 6B); ACC-TP6% (FIG. 6C); ACC-10% (FIG. 6D); ACC-HMP6% (FIG. 6E); ACC-HMP10% (FIG. 6F); ACC-Pyr6% (FIG. 6G) and ACC-Pyr10% (FIG. 6H).
Figure 6B:
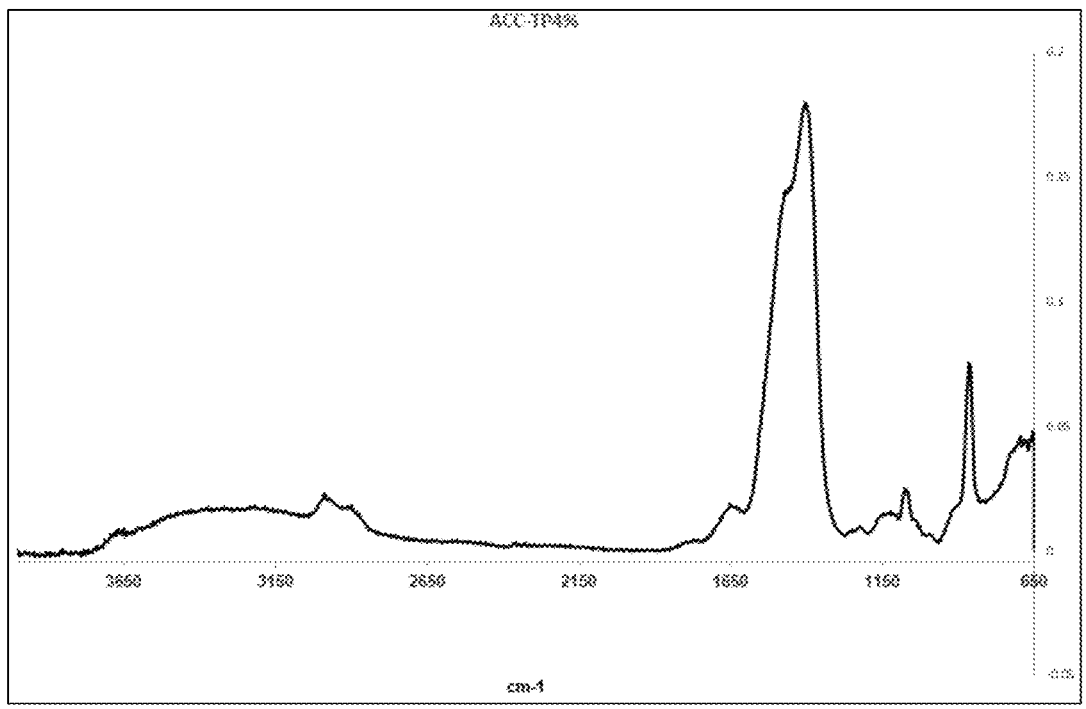
Figure 6C:
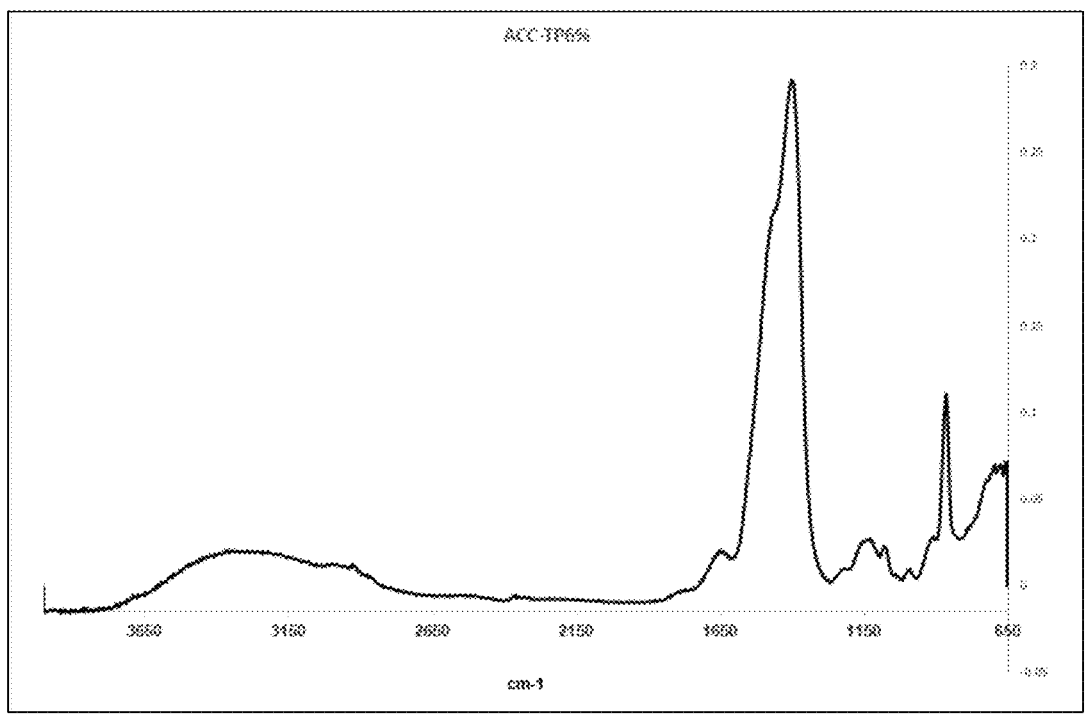
Figure 6D:
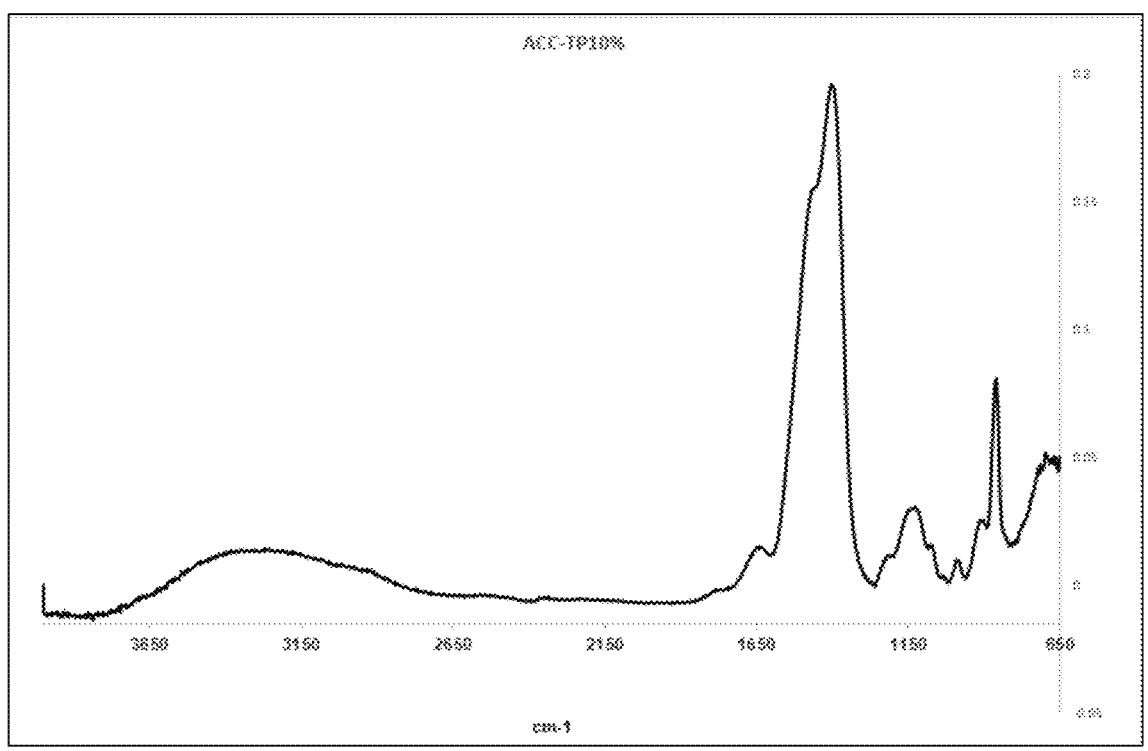
Figure 6E:
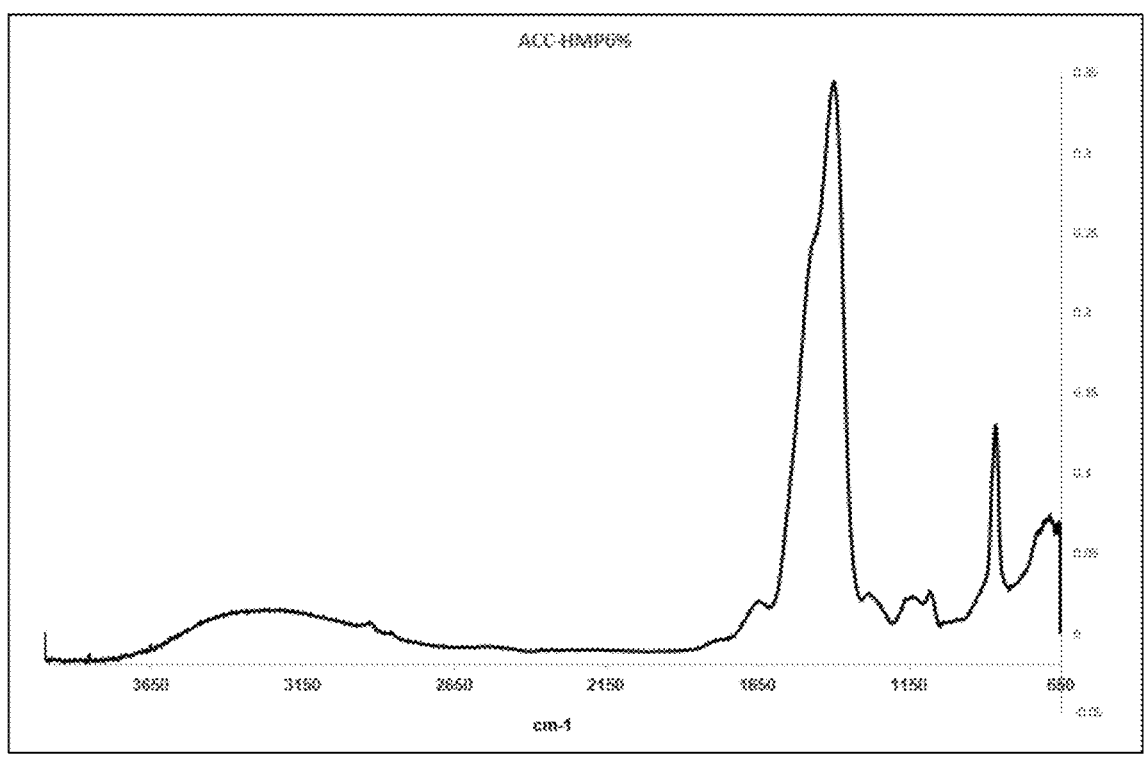
Figure 6F:
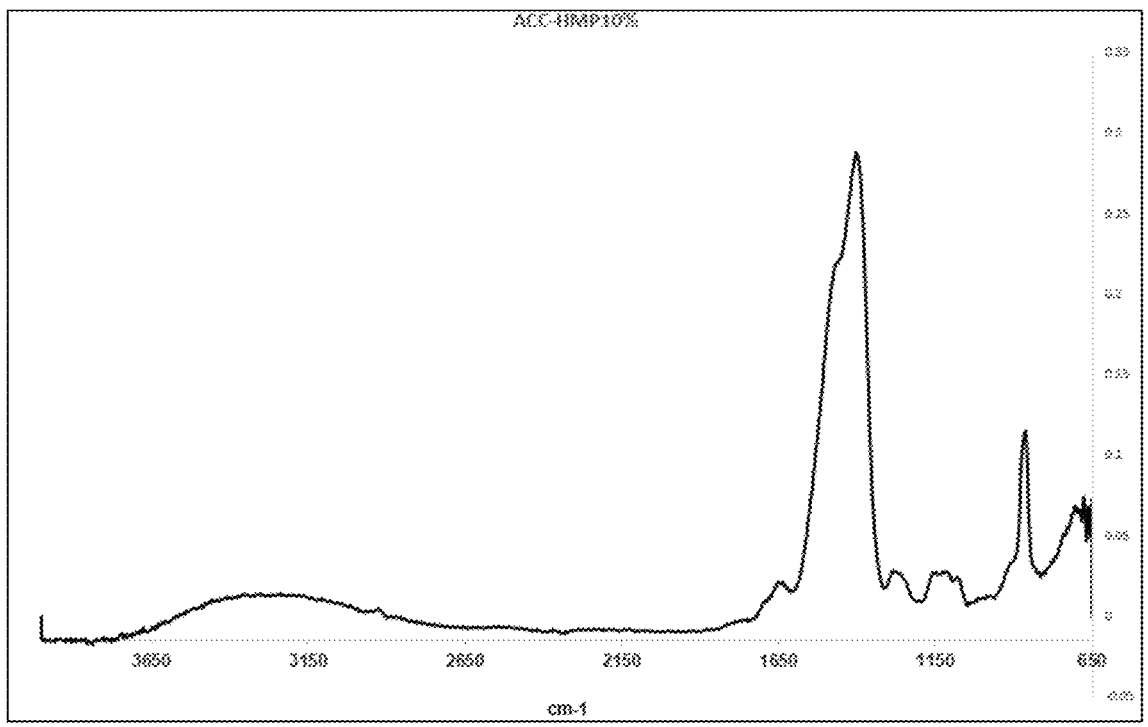
Figure 6G:
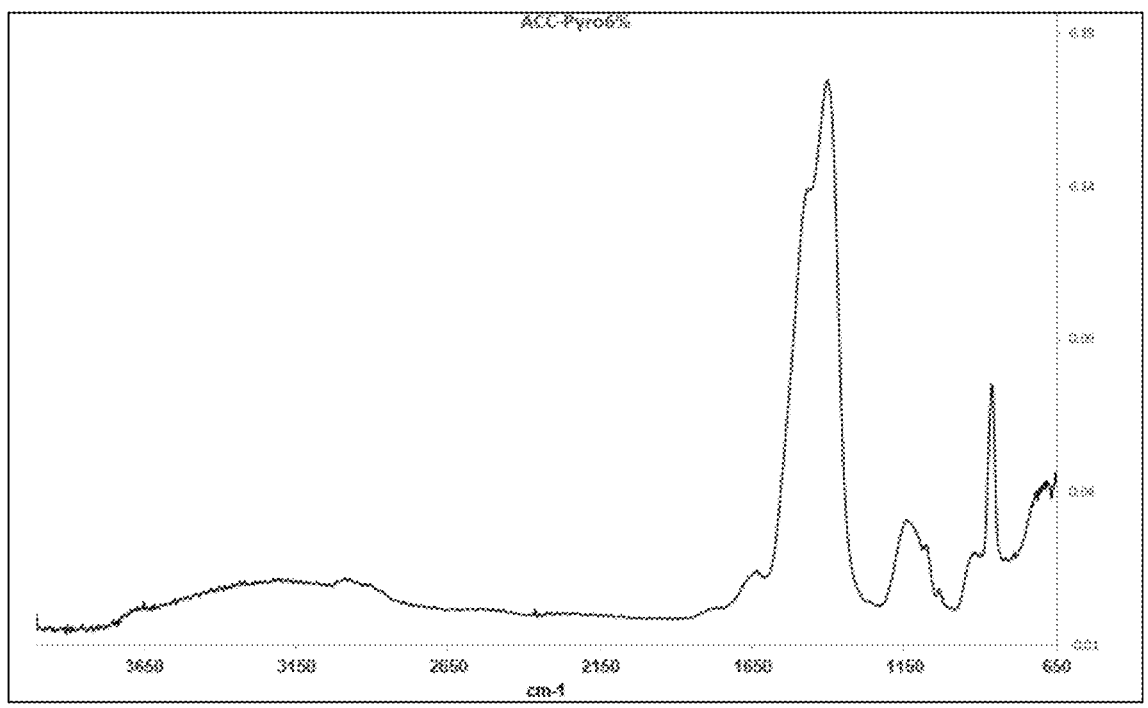
Figure 6H:
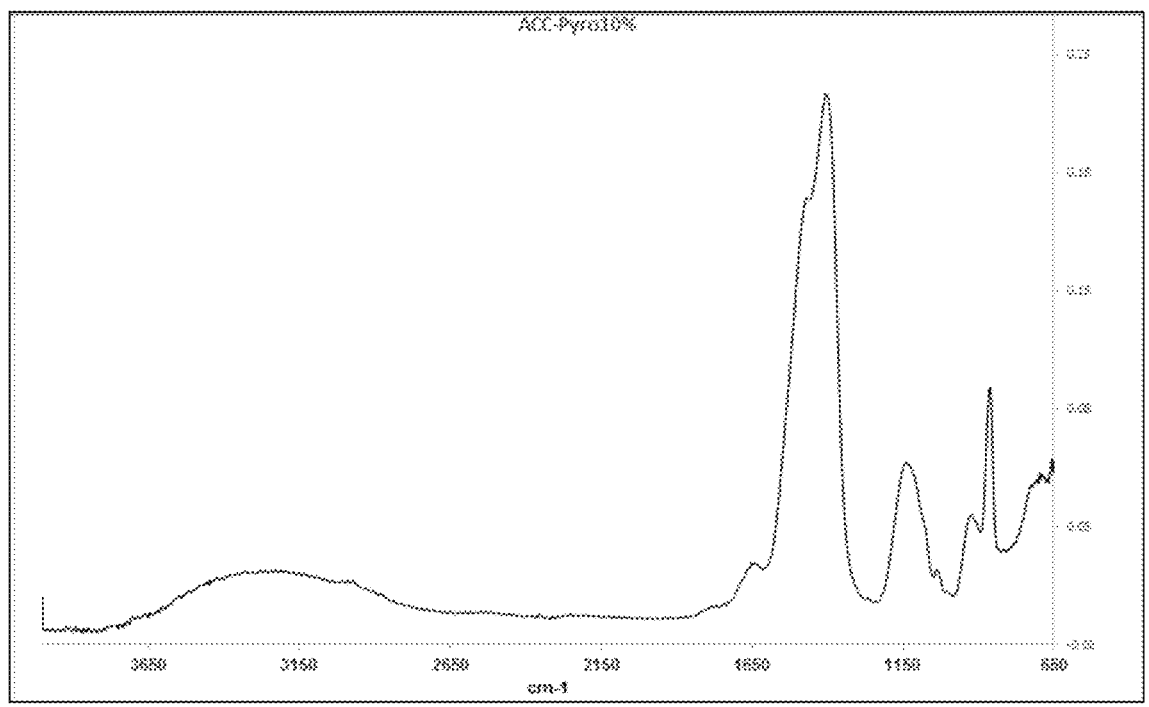
Figure 7:
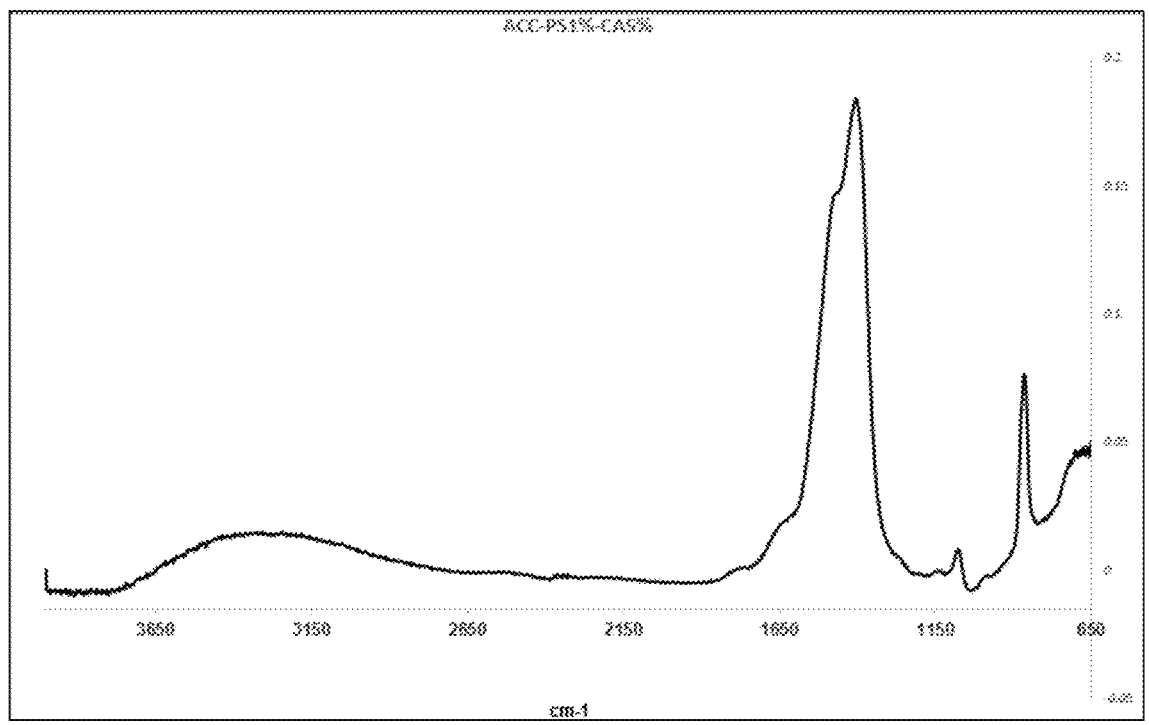
FIG. 7 shows a representative FT-IR absorption spectra of ACC-PS1%-CA5%.

The DSC thermograms of ACC's doped with phosphorus analogs exhibited broad endothermic peak between about 50-250° C. (peak at about 128° C.), which derived from the evaporated water absorbed. The exothermic peak appears at higher temperature of about 367-414° C. for TP (a typical thermogram is presented at FIG. 5.

The crystallization peak of ACC doped with triphosphate at different concentration w/w e.g. 2%, 3%, 4%, 6% shows an increase in the exothermic peaks associated with the temperature of the crystallization: 367° C., 389° C., 400° C. and 414° C. respectively. The DSC analysis indicates that the ACC transformation to the crystalline phase on heating is accelerated when the concentration of stabilizer in ACC is decreased. Hence, the stability of ACC powder on heating depends on the stabilizer concentration—higher concentration—higher stability on heating. This may indicate that ACC is more physically stable at ambient conditions with high stabilizer levels.

Example 14. FT-IR Analysis of ACC Stabilized with Polyphosphates

The FT-IR spectrum of the samples exhibits a strong peak at about 1400 cm$^{-1}$ with a shoulder at about 1470 cm$^{-1}$ and additional medium peak at about 865 cm$^{-1}$ associated to carbonate (CO3)$_2$. All peaks were measured with accuracy of +4 cm$^{-1}$. These peaks show the same intensity for TP, HMP and PS types of stabilizers in ACC and for different quantities of TP (%) in ACC (FIG. 6). This reinforce the observation made in solid state NMR that the carbonyl atom molecule "feels" the same spatial environment in all systems independent of its phosphorous composition or chemical structure.

The small peak at about 1130 cm$^{-1}$ is associated to phosphate. The phosphate peak decrease to a lowest level in case of ACC-PS1%-5% CA and increase gradually to its highest level from 3% to 10% in TP with the maxima corresponding to 10% TP. In FIG. 6 we compared ACC's stabilized with pyrophosphate (FIG. 6G-6H), triphosphate (FIG. 6A-6D), hexametaphosphate (FIG. 6E-6F) at the same stabilizer concentration 10% w/w. Hence, we were able to distinguish between different structures of the stabilizers by observing the intensity of the peaks at about 1130 cm$^{-1}$. In summary: the peak intensity increase reflects the increase percentage of the phosphate stabilizer in ACC when we compare the same phosphate molecule present at different % in ACC or the increase of the phosphate atoms per molecule when we compare different phosphate molecules as stabilizers at the same % in the ACC.

No peak of Ca$_3$(PO4)$_2$, which could arise from a side reaction of CaCl$_2$) with phosphate stabilizer, was detected. No decomposition to Ca$_3$(PO$_4$)$_2$ was observed.

There is also a broad and small peak at about 3300 cm$^{-1}$ which relates to water of the hydrated ACC.

Example 15. Water Content of a Solid ACC Composition Stabilized by Different Stabilizers A thermogravimetric analysis was used to determine a water content of solid ACC preparations stabilized with different stabilizers. TGA Q500 V20.13/Universal V4.5A TA instrument was used with the following heating program: RT—1000° C., heating rate: 10° C./min. N$_2$ flow: 80 mL/min. sample weight: ~10-15 mg, one repetition.

In the TGA curves two apparent weight losses processes are found: the first could be assigned to the water released from RT to about 300° C. and the second at a temperature range of about 500-800° C. to the decomposition of calcium carbonate. It could be estimated that the water content in the ACC-TP samples was about 17-18%. The results are summarized in Table 22.

TABLE 22

Water content of a solid ACC stabilized as measured by TGA

| Sample | Loss On Drying by TGA |
|---|---|
| ACC-TP2% | 18.0% |
| ACC-TP3% | 17.3% |
| ACC-TP4% | 18.3% |
| ACC-TP6% | 18.0% |
| ACC-Pyro-P6% | 17.4% |
| ACC-Pyro-P10% | 15.4% |
| ACC-HMP6% | 17.2% |

Example 16. The Efficacy of ACC in a Mouse Bone Metastasis Model

Purpose and Objectives

The purpose of this study was to assess the potential therapeutic efficacy of ACC stabilized with triphosphate (ACC-TP) on the development and progression of bone metastases in mouse model via intraperitoneal (IP) injections. The model is induced by intra osseous inoculation of 4T1 tumor cells (cells originated from mice mammary gland tumor). Two ACC concentrations were examined. Their efficacy was compared to CaCl2 as a control calcium source and to a common treatment of bone metastases (Bisphosphonate—Alendronic acid).

Test Articles

ACC Administration Via Intraperitoneal Injection (IP):
Preparation of 5 μm Powder of ACC Stabilized with 10% TP and 1% CA Preparation ACC 1% elemental calcium were prepared as following: Calcium solution containing 100 ml of water, 12 g of calcium chloride, 0.12 g of citric acid and 0.06 g of triphosphate were mixed with the carbonate solution containing 100 ml of water and 8.65 g of sodium carbonate to precipitate ACC. The stabilizing solution containing 50 ml of water and 0.6 g of triphosphate were added to the ACC suspension to create stabilized ACC suspension. The ACC was then filtered using a Buchner funnel and the cake was washed with water. Particles powder were obtained following cake drying and milling. Additional milling was perform until reaching the particle size of 5 micrometer.
ACC-TP Compositions in Saline
Two ACC-TP Compositions were Prepared:
  Formulation 1 (referred as ACC1): 0.33 gr ACC powder grinded to 5 μm was added to 100 ml saline to a final concentration of 0.1% Calcium (1 mg/ml).
  Formulation 2 (referred as ACC2): 0.50 gr ACC powder grinded to 5 μm was added to 100 ml saline to a final concentration of 0.15% Calcium (1 mg/ml).
The suspension was mixed using vortex. 200 μl suspension was injected 6 times a week intraperitoneally to mice using 1 ml syringe with 25 G needle.
Bisphosphonate—Alendronic Acid.
  Alendronic acid 100 mg (Sigma cat #A4978) was dissolved in 10 ml saline to a final concentration of 10 mg/ml stock solution. Then a concentration of 0.1 mg/ml was prepared (dilution of 1:100). 120 μl from the 10 mg/ml stock was dissolved in 11,880 μl.
The final concentration that was used was 2 μg/ml. Therefore, 0.6 ml from the 0.1 mg/ml stock solution were dissolved in 29.4 ml saline. The injection solution was made immediately prior to injection. The stock solution was stored at −20° C.
200 μl suspension was injected 3 times a week subcutaneously using 1 ml syringe with 25 G needle.
Calcium Chloride
  0.35 gr of CaCl$_2$), were dissolved in 100 ml saline to a final concentration of 0.1% Calcium (1 mg/ml). 200 μl suspension was injected 6 times a week intraperitoneally to mice using 1 ml syringe with 25 G needle.
Study Design The study was designed in order to assess the potential therapeutic efficacy of ACC-TP via intraperitoneal (IP) injections, on the development and progression of bone metastases in mouse model. The cancer model was induced by Intratibial injections of cancer cells to the Tibia bone. Intratibial injections are used when focusing on the relationships of cancer cells and bone after a tumor has metastasized, thus is considered the most appropriate for such studies.

It was hypothesized that since all tested items comprising calcium and controls were administrated by IP injections, any potential therapeutic effect of ACC would be due to the properties of ACC and not due to the administration route.

Female mice (BALB/c, 9 weeks old) were used for the experiment. Weight variation of animals at study initiation did not exceed ±20% of the mean weight of the gender. Initial body weight was 16-19 gr. The mice were let to acclimatize 5 days prior to the experiment.

Animals were housed in polyethylene cages (6/cage), measuring 35×30×15 cm, with stainless steel top grill facilitating pelleted food and drinking water in plastic bottle; bedding: steam sterilized clean paddy husk (Harlan, Sanichip cat #:2018SC+F) was used and bedding material was changed along with the cage at least once a week.

Amount of food and water consumption were recorded and documented once a week.

Experimental Procedure

The first control or test items administration day was defined as "Day 1". On study day "0" all mice were anesthetized used intraperitoneal injection of Ketamine (80 mg/kg) and Xylazine (5 mg/kg). 4T1 (CRL-2539, B1) cells were injected intratibial into the Tibia in a dose level of 70×10$^3$ cells and dose volume of 10 μl per animal.

The control or test Items comprising calcium were administered intraperitoneally by a 25 G needle, daily (6 days a week) from Day 1 until study termination. The Alendronic acid was administered subcutaneously once a day, 3 days a week.

On the injection day, 15 animals were excluded from the study due to mortality following the anesthesia injection procedure. The mortality of the mice was randomized and was not specific to injection time. Nevertheless, Each group still consisted of sufficient amount of mice for statistical analysis. The number of mice in each group is detailed in Table 23.

TABLE 23

Study design at study execution

| No. Group (n = ) | (Day "0") | Treatment | Dose Volume | Route administration |
|---|---|---|---|---|
| 1F (n = 7) | Intratibial inoculation of 4T1 cells (70 × 103 cells per animal) | Saline | 0.2 ml | 200 μl suspension was injected IP once a day 6 days a week |
| 2F (n = 10) | | ACC1 | | |
| 3F (n = 10) | | ACC2 | | |
| 4F (n = 9) | | CaCl2 | | |
| 5F (n = 9) | | Bisphosphonate - Alendronic acid | | Subcutaneous injection once a day, 3 days a week |

The Study was terminated at "Day 27" for groups 1F, 2F, 5F. and at "Day 23" for groups 3F, 4F. At study termination (Day 23 and Day 27), animals were anesthetized by CO2 asphyxiation.

Observations and Examinations

The following measurements and observations were recorded: (i) Mortality and morbidity (daily); (ii) Clinical signs observations (twice a week); (iii) Body weight measurements (once a week and at study termination); (iv) Radiographic analysis; and (v) Amount of food and water consumption (once a week).

Clinical Observation

Up to study termination, all animals were observed for clinical signs twice a week.

Observations were performed for any changes in skin, fur, eyes, mucous membranes, respiratory, occurrence of secretions and excretions (e.g. diarrhea). Changes in gait, posture and response to handling, as the presence of bizarre behavior, tremors, convulsions, sleep and coma were also included.

All observed abnormalities, toxic signs, moribund condition and pre-terminal deaths were documented.

Animals that were humanely sacrificed during the test are considered for the interpretation of test results as animals that died during the test.

Radiographic Analysis

X-ray monitoring were performed at Day "0" and Day "20" (X-ray generator Girth 8015).

The digital X-rays (of day 20) were examined for the presence of osteolytic lesions specifically in the left Tibia bone (inoculation site).

Results

Tumor development in mice was analyzed by radiographic micrograph examination at days 0 and day 20 and showed which mice developed tumor. The bone abnormality was detected by thinning of the bone, decreased density and discontinuity through the bone length in the x-ray micrographs. Mice that did not develop any tumor throughout the study period were therefore, excluded from the final statistics.

At day 20, all animals were found with severe swelling of the soft tissue surrounding the bone. This was correlated to the severe damage identified by the bone X-ray micrograph. In addition, the mortality rate increased and severe clinical signs i.e., piloerection, Dyspnea, hunch and limping continued to appear among the animals.

Based on the above results, it was decided to terminate the study at day 23 for groups 4F and 3F which were treated with $CaCl_2$) and ACC2, respectively, and at day 27 following injection for groups 1F, 2F and 5F that had been treated with saline, ACC1 and ALN respectively.

Figure 8:
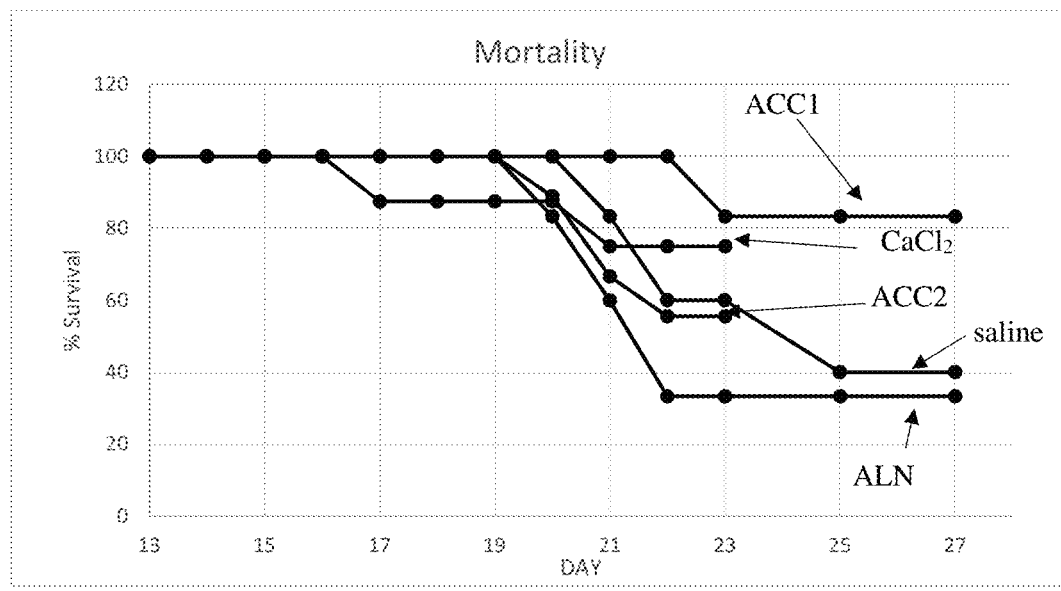
FIG. 8 shows mortality of mice from day 13-27 following 4T1 cells injection according to Example 16.

Mice mortality rate is presented in FIG. 8 Group number 2F named ACC1 which has been treated with 0.1% calcium had the highest survival rate troughout all of the study duration. Up to day 22, no mice had deceased from ACC1 group. Group number 1F, saline, which was not treated had no mice mortality up to day 20. However, its survival rate is much lower and by the end of day 27 had 40% survival vs. 80% survival in ACC1. Group ACC2 where mice were treated with 0.15% Calcium had no mice deceased up to day 19 and demonstrated a similar survival rate relative to the Saline treated group up to day 23. In the group that was treated with ALN, a bisphosphonate no mice had deceased up to day 19 also, but it survival rate is lower. The group that was treated with $CaCl_2$) had mice deceased as early as day 16. Its survival percentages however, were higher than 75% up to day 23 of study duration.

Figure 9:
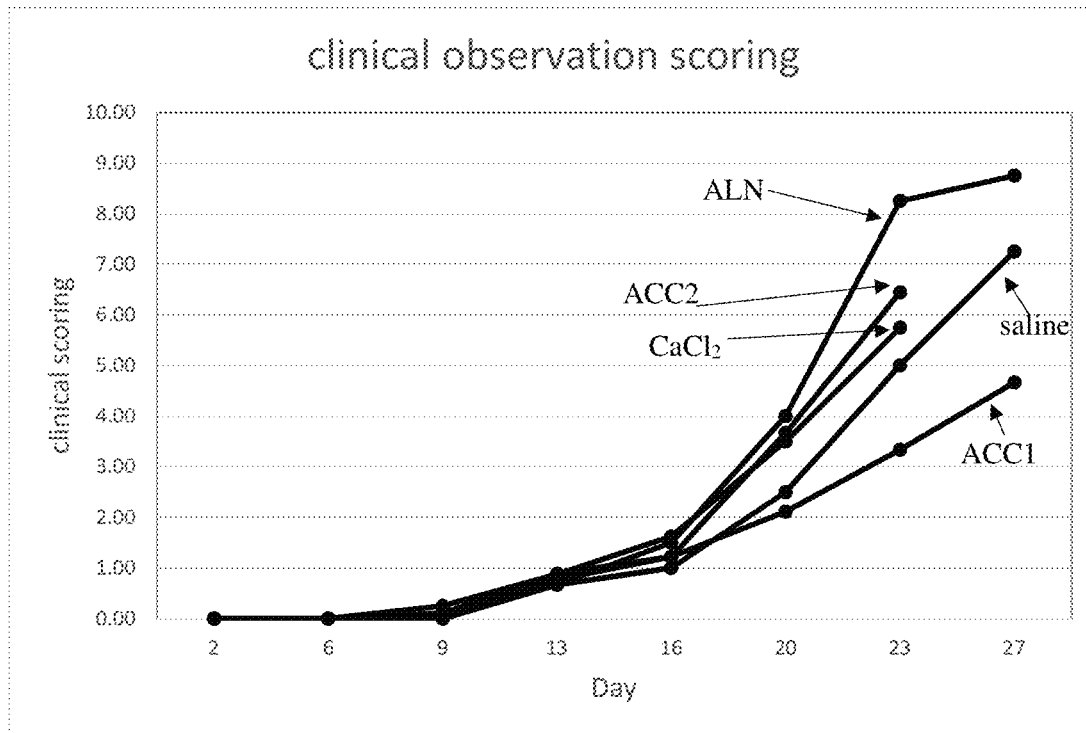
FIG. 9 shows the clinical signs scoring from day 0-27 following 4T1 cells injection according to Example 16.

The above results trend have repeated in the clinical signs scoring as well (FIG. 9). High scoring of clinical signs correlates to more clinical signs detection and low scoring correlates to less. ACC1 group that was treated with 0.1% Calcium originated from ACC had the lowest scoring of clinical signs throughout all study duration. Group number 1F, saline, which was not treated had a similar scoring up to day 20, however from day 20 to 27 demonstrated a fast declaration in mice clinical signs. Group ACC2 and $CaCl_2$) clinical signs had similar behaviors when compared one to the other which also correlates to the survival rates. Additional correlation was found in the ALN group that had the highest scoring of clinical signs i.e. the worst health condition of the mice in the group.

As can be seen Group 2F which has been treated with ACC1 demonstrated consistently up to day 27 the lowest clinical sign scoring with comparison to all other groups.

Figure 10:
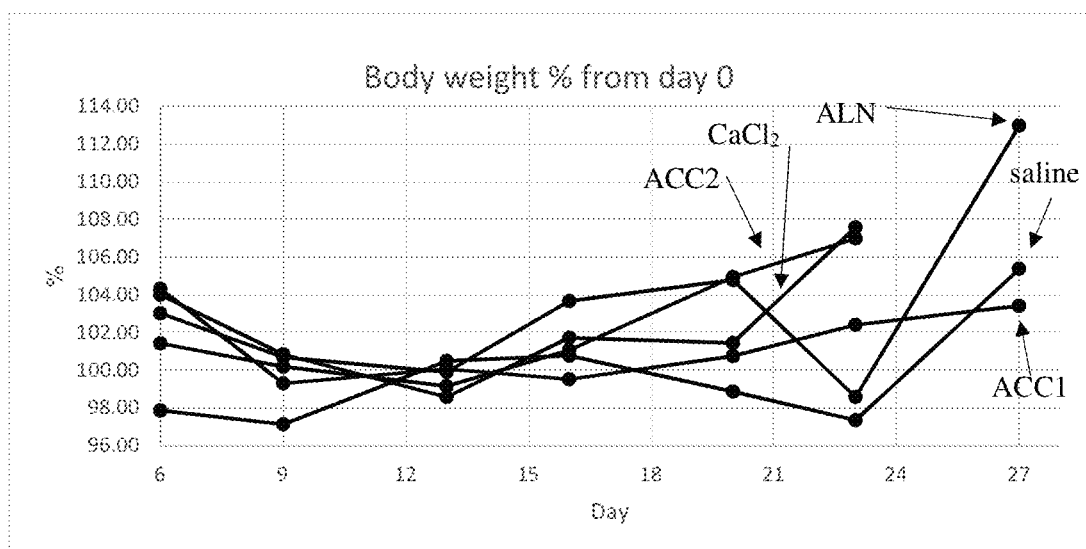
FIG. 10 shows the Body Weight of the mice in different groups according to Example 16.

Body Weight percentages of all groups demonstrated a similar body weight balances during the experiment duration with no significant differences between the groups as can be seen in FIG. 10. The fluctuations line of the body weight graph is characterized for all groups and probably originates from body weight loss prior to mice death, thus once a mice was deceased and was excluded from the statistics a misleading trend up in the graph is observed. Since this is a body weight percentages average, the small number of items in a group demonstrate a larger the effect of the fluctuations.

CONCLUSION

The formulation that demonstrated the best performance is ACC1. This group was administrated with 0.1% calcium originated from ACC-TP. The group demonstrated consistently the highest survival rate and the lowest clinical signs. The strong correlation between both indications emphasis the positive therapeutic effect of ACC1 on mice with 4T1 tumor cells.

Administration of ACC2 formulation did not demonstrated the same positive therapeutic effect as ACC formula 1. ACC2 contained 0.15% elementary calcium. Although, the lethal calcium dose is twice of the administered amount, it may be that the dose was too high, resulted in the health deterioration.

The formulation that demonstrated the worst performance is Bisphosphonate—Alendronic acid. Bisphosphonates based drugs are administrated to oncology patients as part of their treatment. There is mixed evidence regarding whether or not bisphosphonates improve mice survival (Ben-Aharon I et al. (2013) PLOS ONE 8 (8)).

$CaCl_2$) formula had 0.1% elementary calcium, similar amount of calcium as ACC1 contained. However, this groups demonstrated a lower survival percentage with higher number of clinical signs. It appears that not only the calcium ion is responsible for therapeutic effect in the ACC, since we do not see the same effect in the calcium chloride. This may be either due to an additional mechanism of the ACC molecule in its amorphous state, or to the carbonate ion.

Example 17. ACC Administration Via Inhalation Combined with an Oral Administration to Cancer Patients A single arm, open label, compassionate clinical supportive care study to assess the welfare improvement of terminally ill, late advanced, solid cancer patients (with or without lung involvement) by Amorphous Calcium Carbonate (ACC) treatment, administered orally and concomitantly by inhalation is carried out.

Study Population:
20 subjects with solid malignancies, with or without lung metastases, who failed anti-cancer treatment are enrolled.
Dosage Regiment
Oral Dosage Form
DENSITY is formulated as a caplet containing ACC, as well as Cellulose Microcrystalline, Plasdone K-25, Stearic Acid, and Magnesium Stearate as inactive excipients.

Each DENSITY caplet contains 666 mg ACC as API (i.e. Amorphous $CaCO_3$+Aerosil+drug substance stabilizers) which corresponds to 500 mg $CaCO_3$, and equivalent to 200 mg elemental calcium (hereinafter the dose refers to the amount of elemental calcium). Up to nine DENSITY tablets are administered per day for a maximal calcium dose of 1,800 mg/day.

Inhalation Dosage Form
Inhalation formulation is formed from 1% ACC (i.e. 0.3% calcium)+water for injection, as a sterile suspension (8 mL, twice daily).

All subjects start at a DENSITY dose of 600 mg per day and are escalated to a total daily dose of up to 1,800 mg and Inhaled 1% ACC in 8 mL water, twice daily.

Study Procedures
Twenty (20) subjects diagnosed with late stage solid cancer (with or without lung involvement) who failed other anti-cancer treatment are enrolled and administered with both oral ACC up to 1,800 mg in the form of DENSITY in addition to an inhaled solution of 1% ACC stabilized with a polyphosphate.

Starting Dose: Oral ACC 600 mg (3 tablets, one tablet taken three times a day) scaled up by 200 mg every second day until reaching a maximum dose of 1,800 mg. ACC Inhaled; 1% ACC in 8 mL saline once daily and escalated after 3 days to a maximum dose of Inhaled 1% ACC in 8 mL saline twice daily The calcium levels are evaluated using serum calcium corrected for albumin (CA) value tests before each dose escalation.

Endpoints

Compassionate clinical supportive care program evaluating the improvement of subject's welfare as determined by assessing:

Reduction in pain based on VAS score
Opiate withdrawal by dose and/or numbers of analgesic products
Functional improvement based on ECOG PS
Survival as compared to physician estimation or hospice historical data
Change in arterial oxygen saturation as determined by pulse oximeter
Evaluation Endpoints (Safety):
Percent of subjects with hypercalcemia DLTs per dose
Percent of subjects with any DLTs per dose
Vital Signs
Height and weight are measured as per protocol. (Insert the position and times when such evaluations are performed—e.g. X minutes after rest).

Throughout all study phases, vital signs (temperature, peripheral arterial blood pressure, heart rate and respiratory rate), are obtained after the subject has rested for 5 minutes.

Temperature is obtained by thermometer throughout all study phases.

Peripheral arterial blood pressure (systolic, diastolic) is obtained by sphygmomanometry throughout all study phases.

Heart rate is obtained using calibrated standard measuring devices.

Respiratory rate is obtained by observing chest excursions for a minimum of 30 seconds.

The physical examination is conducted on all major organ systems, excluding rectal and pelvic examinations. Weight and height is measured and recorded as per protocol.

The Investigator will use clinical judgment when determining the clinical significance of any physical examination finding.
Physical Examination
A physical examination is performed and documented by the investigator or a qualified designee. Any abnormal findings, assessed by the investigator as clinically significant, should be recorded in the relevant CRF modules (e.g. adverse event, medical history)

In monitoring the patient for positive and negative results one or more of the following is accepted as improvement:
Functional improvement based on ECOG PS;
Prolonged survival as compared to at least one of physician estimation or hospice historical data
Increase in arterial oxygen saturation as determined by pulse oximeter
Pain reduction (VAS scale), in at least one of intensity, frequency and duration.

In selecting an ACC dosing regimen, blood calcium measurements or changes therein may be used as a consideration according to which to adjust a dosage for a given patient. For example an increase or even development of hypercalcemia may cause a reduction of daily dosage and/or in spreading the ACC dose to smaller doses taken more often.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:
1. A method of treating a disease or a condition responsive to a calcium carbonate treatment, comprising administering an effective amount of a composition, comprising:

amorphous calcium carbonate (ACC) particles comprising a bisphosphonate or pharmaceutically acceptable salts thereof as a stabilizer that forms a non-disintegratable part of the ACC particles;

about 5 wt % to about 30 wt % water;

wherein a molar ratio between P atoms of the stabilizer and Ca atoms of the ACC (P:Ca molar ratio) is at least about 1:90;

wherein the composition is stable for at least 7 days; and wherein the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious disease, and dental disease.

2. The method of claim 1, wherein the composition is characterized by at least one of the following:

(i) the P:Ca molar ratio is about 1:90 to 1:1, about 1:40 to about 1:1, or 1:25 to about 1:5;

(ii) the bisphosphonate is selected from the group consisting of etidronic acid, zoledronic acid, medronic acid, alendronic acid and pharmaceutically acceptable salts thereof;

(iii) the composition comprises about 10 wt % to about 20 wt % water;

(iv) the composition is stable for at least, 1 month, 3 months, 6 months or 1 year;

(v) the composition is in the form of a powder or a suspension;

(vi) the composition comprises less than 1%, 5%, 10% or 30% of crystalline calcium carbonate out of the total calcium carbonate;

(vii) the composition is devoid of organic solvents;

(viii) the composition further comprises one or more organic acids; or (ix) the composition is formulated as a pharmaceutical, nutraceutical or cosmetic composition, as a food supplement or a medical food.

3. The method of claim 2, wherein the suspension is an aqueous suspension.

4. The method of claim 1, wherein the stabilizer is added during the preparation of ACC and therefore constitutes an integral part of the ACC particles.

* * * * *